United States Patent
Li et al.

(10) Patent No.: US 7,307,156 B2
(45) Date of Patent: *Dec. 11, 2007

(54) CRYSTAL FORMS OF AZITHROMYCIN

(75) Inventors: Zheng J. Li, Quaker Hill, CT (US); Andrew V. Trask, Stonington, CT (US); Joseph E. Mertz, Baltic, CT (US)

(73) Assignee: Pfizer Inc., New York, NY (US)

( * ) Notice: Subject to any disclaimer, the term of this patent is extended or adjusted under 35 U.S.C. 154(b) by 192 days.

This patent is subject to a terminal disclaimer.

(21) Appl. No.: 10/650,252

(22) Filed: Aug. 27, 2003

(65) Prior Publication Data

US 2004/0043944 A1    Mar. 4, 2004

Related U.S. Application Data

(63) Continuation of application No. 10/152,106, filed on May 21, 2002, now Pat. No. 6,977,243.

(60) Provisional application No. 60/343,041, filed on Dec. 21, 2001, provisional application No. 60/297,741, filed on Jun. 12, 2001, provisional application No. 60/292,565, filed on May 22, 2001.

(51) Int. Cl.
*A61K 31/70* (2006.01)
*C07H 17/08* (2006.01)

(52) U.S. Cl. .................................. 536/7.4; 514/29

(58) Field of Classification Search ................ 536/7.4, 536/6.4; 514/29
See application file for complete search history.

(56) References Cited

U.S. PATENT DOCUMENTS

| | | | |
|---|---|---|---|
| 4,328,334 A | 5/1982 | Kobrehel et al. | 536/7.4 |
| 4,465,674 A | 8/1984 | Bright et al. | 424/180 |
| 4,474,768 A | 10/1984 | Bright | 424/180 |
| 4,517,359 A | 5/1985 | Kobrehel et al. | 536/7.4 |
| 4,963,531 A | 10/1990 | Remington | 514/29 |
| 6,245,903 B1 | 6/2001 | Karimian et al. | 536/7.4 |
| 6,268,489 B1 | 7/2001 | Allen et al. | 536/7.4 |
| 6,365,574 B2 * | 4/2002 | Singer et al. | 514/29 |
| 6,420,537 B1 * | 7/2002 | Bosch et al. | 536/7.4 |
| 6,451,990 B1 | 9/2002 | Bayod Jasanada et al. | 536/7.4 |
| 6,528,492 B1 | 3/2003 | de la Torre Garcia et al. | 514/29 |
| 6,586,576 B2 * | 7/2003 | Aronhime et al. | 536/7.4 |
| 6,861,413 B2 * | 3/2005 | Li et al. | 514/29 |
| 2001/0047089 A1 | 11/2001 | Aronhime et al. | |
| 2002/0111318 A1 | 8/2002 | Rengaraju | |

FOREIGN PATENT DOCUMENTS

| | | |
|---|---|---|
| CA | 2245398 | 2/1998 |
| CN | 1093370 | 12/1994 |
| CN | 1114960 | 1/1996 |
| CN | 1161971 | 10/1997 |
| CN | 11961971 | 10/1997 |
| EP | 0298650 | 6/1988 |
| EP | 0941999 | 9/1999 |
| EP | 1103558 | 2/2000 |
| EP | 1103558 | 5/2001 |
| EP | 1234833 | 8/2002 |
| WO | WO9804574 | 2/1998 |
| WO | WO0014099 | 3/2000 |
| WO | WO0032203 | 6/2000 |
| WO | WO0100640 | 1/2001 |
| WO | WO0149697 | 7/2001 |
| WO | WO0187912 | 11/2001 |
| WO | WO0207736 | 1/2002 |
| WO | WO0209540 | 2/2002 |
| WO | WO0209640 | 2/2002 |
| WO | WO0210181 | 2/2002 |
| WO | WO0215842 | 2/2002 |
| WO | WO0242315 | 5/2002 |
| WO | WO02085898 | 10/2002 |
| WO | WO0187912 | 11/2002 |
| WO | WO03032922 | 4/2003 |

OTHER PUBLICATIONS

Chemical Abstracts, vol. 124, No. 3 (Jan. 15, 1996) Abstract No. 29525, Abstract of CN1093370.
Chemical Abstracts, vol. 124, No. 3 (Jan. 15, 1996) Abstract No. 29525, Abstract of CN1093370.

* cited by examiner

*Primary Examiner*—Elli Peselev
(74) *Attorney, Agent, or Firm*—Gregg C. Benson; B. Timothy Creagan; Lance Y. Liu

(57) ABSTRACT

The invention relates to novel crystal forms of azithromycin, an antibiotic useful in the treatment of infections.

12 Claims, 33 Drawing Sheets

CRYSTAL FORMS OF AZITHROMYCIN

This application is a continuation of U.S. Ser. No. 10/152,106, filed May 21, 2002, now U.S. Pat. No. 6,977,243 which is a non provisional of Provisional Applications No. 60/343,041, filed Dec. 21, 2001, No. 60/297,741, filed Jun. 12, 2001, and No. 60/292,565, filed May 22, 2001.

BACKGROUND OF THE INVENTION

This invention relates to crystal forms of azithromycin. Azithromycin is sold commercially and is an effective antibiotic in the treatment of a broad range of bacterial infections. The crystal forms of this invention are likewise useful as antibiotic agents in mammals, including man, as well as in fish and birds.

Azithromycin has the following structural formula:

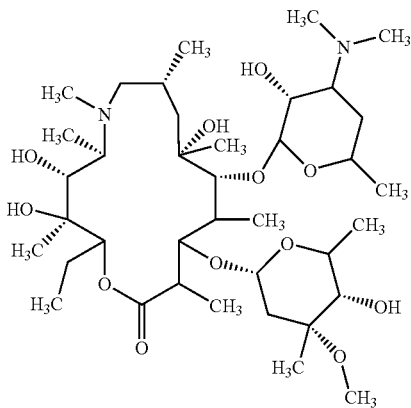

Azithromycin is described and claimed in U.S. Pat. Nos. 4,517,359 and 4,474,768. It is also known as 9-deoxo-9a-aza-9a-methyl-9a-homoerythomycin A.

Other patents or patent applications which directly or indirectly cover azithromycin include: EP 298,650 which claims azithromycin dihydrate; U.S. Pat. No. 4,963,531 which claims a method of treating a strain of *Toxoplasma gondii* species; U.S. Pat. No. 5,633,006 which claims a chewable tablet or liquid suspension pharmaceutical composition having reduced bitterness; U.S. Pat. No. 5,686,587 which claims an intermediate useful in the preparation of azithromycin; U.S. Pat. No. 5,605,889 which claims an oral dosage form that reduces the "food effect" associated with the administration of azithromycin; U.S. Pat. No. 6,068,859 which claims a controlled dosage form containing azithromycin; U.S. Pat. No. 5,498,699 which claims a composition containing azithromycin in combination with bivalent or trivalent metals; EP 925,789 which claims a method of treating eye infections; Chinese patent application CN 1123279A which relates to water soluble salts of azithromycin; Chinese patent application CN 1046945C which relates to azithromycin sodium dihydrogenphosphate double salts; Chinese patent application CN 1114960A which relates to azithromycin crystals, Chinese patent application CN 1161971A which relates to azithromycin crystals; Chinese patent application CN 1205338A which relates to a method of preparing water soluble salts of azithromycin; International Publication WO 00/32203 which relates to an ethanolate of azithromycin; and European patent application EP 984,020 which relates to an azithromycin monohydrate isopropanol clathrate.

SUMMARY OF THE INVENTION

The present invention relates to crystal forms of azithromycin. As used herein, the term "crystal form(s)" or "form(s)", unless otherwise noted, means one or more crystal forms of azithromycin.

In particular, the present invention relates to a crystal form of azithromycin wherein said crystal form is selected from forms C, D, E, F, G, H, J, M, N, O, P, Q and R wherein said forms are as defined herein. Forms F, G, H, J, M, N, O, and P belong to family I azithromycin and belong to a monoclinic P2$_1$ space group with cell dimensions of a=16.3±0.3 Å, b=16.2±0.3 Å, c=18.4±0.3 Å and beta=109±2°. Forms C, D, E and R belong to family II azithromycin and belong to an orthorhombic P2$_1$2$_1$2$_1$ space group with cell dimensions of a=8.9±0.4 Å, b=12.3±0.5 Å and c=45.8±0.5 Å. Form Q is distinct from families I and II.

Form F azithromycin is of the formula $C_{38}H_{72}N_2O_{12} \cdot H_2O \cdot 0.5C_2H_5OH$ in the single crystal structure, being azithromycin monohydrate hemi-ethanol solvate. Form F is further characterized as containing 2–5% water and 1–4% ethanol by weight in powder samples and having powder X-ray diffraction 2θ peaks as defined in Table 9. The $^{13}C$ ssNMR (solid state Nuclear Magnetic Resonance) spectrum of form F has two chemical shift peaks at approximately 179±1 ppm, those being 179.5±0.2 ppm and 178.6±0.2 ppm, a set of five peaks between 6.4 to 11.0 ppm, and ethanol peaks at 58.0±0.5 ppm and 17.2±0.5 ppm. The solvent peaks can be broad and relatively weak in intensity.

The invention also relates to substantially pure form F azithromycin, form F azithromycin substantially free of form G azithromycin and form F azithromycin substantially free of azithromycin dihydrate.

The invention further relates to methods of preparing form F azithromycin by treating azithromycin with ethanol to complete dissolution at 40–70° C. and cooling with reduction of ethanol or addition of water to effect crystallization. Also included are methods of making substantially pure form F azithromycin, form F azithromycin substantially free of form G azithromycin and form F azithromycin substantially free of azithromycin dihydrate.

Form G azithromycin is of the formula $C_{38}H_{72}N_2O_{12} \cdot 1.5H_2O$ in the single crystal structure, being azithromycin sesquihydrate. Form G is further characterized as containing 2.5–6% water and <1% organic solvent(s) by weight in powder samples and having powder X-ray diffraction 2θ peaks as defined in Table 9. The $^{13}C$. ssNMR spectrum of form G has one chemical shift peak at approximately 179±1 ppm, being a peak at 179.5±0.2 ppm (splitting<0.3 ppm may present), and a set of five peaks between 6.3 to 11.0 ppm.

The invention also relates to substantially pure form G azithromycin, and form G azithromycin substantially free of azithromycin dihydrate.

The invention further relates to methods of preparing substantially pure form G azithromycin, and form G azithromycin substantially free of azithromycin dihydrate by treating azithromycin with a mixture of methanol and water or acetone and water to complete dissolution at 40–60° C. and cooling to effect crystallization.

Form H azithromycin is of the formula $C_{38}H_{72}N_2O_{12} \cdot H_2O \cdot C_3H_8O_2$ being azithromycin monohydrate hemi-1,2 propanediol solvate.

Form J azithromycin is of the formula $C_{38}H_{72}N_2O_{12} \cdot H_2O \cdot 0.5C_3H_7OH$ in the single crystal structure, being azithromycin monohydrate hemi-n-propanol solvate. Form J is further characterized as containing 2–5% water and 1–5% 1-propanol by weight in powder samples and having powder X-ray diffraction 2θ peaks as defined in Table 9. The $^{13}$C ssNMR spectrum of form J has two chemical shift peaks at approximately 179±1 ppm, those being 179.6±0.2 ppm and 178.4±0.2 ppm, a set of five peaks between 6.6 to 11.7 ppm and an n-propanol peak at 25.2±0.4 ppm. The solvent peak can be broad and relatively weak in intensity.

The invention further relates to methods of preparing form J by treating azithromycin with n-propanol to complete dissolution at 25–55° C. and cooling with addition of water to effect crystallization.

Form M azithromycin is of the formula $C_{38}H_{72}N_2O_{12} \cdot H_2O \cdot 0.5C_3H_7OH$, being azithromycin monohydrate hemi-isopropanol solvate. Form M is further characterized as containing 2–5% water and 1–4% 2-propanol by weight in powder samples and having powder X-ray diffraction 2θ peaks as defined in Table 9. The $^{13}$C ssNMR spectrum of form M has one chemical shift peak at approximately 179±1 ppm, being 179.6±0.2 ppm, a peak at 41.9±0.2 ppm and a set of six peaks between 6.9 to 16.4 ppm and an isopropanol peak at 26.0±0.4 ppm. The solvent peak can be broad and relatively weak in intensity.

The invention also relates to substantially pure form M azithromycin, form M azithromycin substantially free of form G azithromycin and form M azithromycin substantially free of azithromycin dihydrate.

The invention further relates to methods of preparing substantially pure form M azithromycin, form M azithromycin substantially free of form G azithromycin and form M azithromycin substantially free of azithromycin dihydrate by treating azithromycin with isopropanol to complete dissolution at 40–60° C. and reduction of isopropanol followed by cooling or cooling followed by addition of water to effect crystallization.

Form N azithromycin is a mixture of isomorphs of Family I. The mixture may contain variable percentages of isomorphs, F, G, H, J, M and others, and variable amounts of water and organic solvents, such as ethanol, isopropanol, n-propanol, propylene glycol, acetone, acetonitrile, butanol, pentanol, etc. The weight percent of water can range from 1–5% and the total weight percent of organic solvents can be 2–5% with each solvent content of 0.5 to 4%. The samples of form N display all characteristic peaks of members of Family I in various proportions. Form N may be characterized as 'mixed crystals' or 'crystalline solid solutions' of Family I isomorphs.

Form N displays chemical shifts as a combination of isomorphs in Family I. The peaks may vary in chemical shift ppm within ±0.2 ppm and in relative intensities and width due to the mixing of variable proportion of isomorphs contained in the form N crystalline solid solution.

Form P azithromycin is of the formula $C_{38}H_{72}N_2O_{12} \cdot H_2O \cdot 0.5C_5H_{12}O$ being azithromycin monohydrate hemi-n-pentanol solvate.

Form Q azithromycin is of the formula $C_{38}H_{72}N_2O_{12} \cdot H_2O \cdot 0.5C_4H_8O$ being azithromycin monohydrate hemi-tetrahydrofuran solvate.

Form R azithromycin is of the formula $C_{38}H_{72}N_2O_{12} \cdot H_2O \cdot C_5H_{12}O$ being azithromycin monohydrate mono-methyl tert-butyl ether solvate.

Form D azithromycin is of the formula $C_{38}H_{72}N_2O_{12} \cdot H_2O \cdot C_6H_{12}$ in its single crystal structure, being azithromycin monohydrate monocyclohexane solvate. Form D is further characterized as containing 2–6% water and 3–12% cyclohexane by weight in powder samples and having representative powder X-ray diffraction 2θ peaks as defined in Table 9. The $^{13}$C ssNMR spectrum of form D displays has one chemical shift peak at approximately 179±1ppm, being 178.1±0.2ppm and peaks at 103.9±0.2ppm, 95.1±0.2ppm, 84.2±0.2 ppm, and a set of 3 peaks between 8.4 to 11 ppm.

The invention further relates to methods of preparing form D by slurrying azithromycin dihydrate with cyclohexane.

Form E azithromycin is of the formula $C_{38}H_{72}N_2O_{12} \cdot H_2O \cdot C_4H_8O$ being azithromycin monohydrate mono-tetrahydrofuran solvate.

The invention further relates to azithromycin in an amorphous state and a method of preparing amorphous azithromycin that comprises the removal of water and/or solvents from the azithromycin crystal lattice. The X-ray diffraction powder pattern for amorphous azithromycin displays no sharp 2θ peaks but has two broad rounded peaks. The first peak occurs between 4° and 13°. The second peak occurs between 13° and 25°.

The invention also relates to pharmaceutical compositions for the treatment of a bacterial infection or a protozoa infection in a mammal, fish, or bird which comprises a therapeutically effective amount of the crystalline compounds referred to above, or amorphous azithromycin, and a pharmaceutically acceptable carrier.

The invention also relates to a method of treating a bacterial infection or a protozoa infection in a mammal, fish, or bird which comprises administering to said mammal, fish or bird a therapeutically effective amount of the crystalline compounds referred to above, or amorphous azithromycin.

The present invention also relates to methods of preparing crystal forms of azithromycin which comprise the slurrying of azithromycin in an appropriate solvent or the dissolution of azithromycin in a heated organic solvent or organic solvent/water solution and precipitating the crystalline azithromycin by cooling the solution with reduction of solvent volume or by dissolving azithromycin in a solvent or solvent mixture and precipitating crystalline azithromycin by the addition of water to the solution. Azithromycin in amorphous state is prepared by heating crystalline azithromycin in a vacuum.

The term "treatment", as used herein, unless otherwise indicated, means the treatment or prevention of a bacterial infection or protozoa infection as provided in the method of the present invention, including curing, reducing the symptoms of or slowing the progress of said infection. The terms "treat" and "treating" are defined in accord the foregoing term "treatment".

The term "substantially free" when referring to a designated crystalline form of azithromycin means that there is less than 20% (by weight) of the designated crystalline form(s) present, more preferably, there is less than 10% (by weight) of the designated form(s) present, more preferably, there is less than 5% (by weight) of the designated form(s) present, and most preferably, there is less than 1% (by weight) of the designated crystalline form(s) present. For instance, form F azithromycin substantially free of azithromycin dihydrate means form F with 20% (by weight) or less of azithromycin dihydrate, more preferably, 10% (by weight) or less of azithromycin dihydrate, most preferably, 1% (by weight) of azithromycin dihydrate.

The term "substantially pure" when referring to a designated crystalline form of azithromycin means that the designated crystalline form contains less than 20% (by weight) of residual components such as alternate polymorphic or isomorphic crystalline form(s) of azithromycin. It is preferred that a substantially pure form of azithromycin contain less than 10% (by weight) of alternate polymorphic or isomorphic crystalline forms of azithromycin, more preferred is less than 5% (by weight) of alternate polymorphic or isomorphic crystalline forms of azithromycin, and most preferably less than 1% (by weight) of alternate polymorphic or isomorphic crystalline forms of azithromycin.

The term "substantially in the absence of azithromycin dihydrate" when referring to bulk crystalline azithromycin or a composition containing crystalline azithromycin means the crystalline azithromycin contains less than about 5% (by weight) azithromycin dihydrate, more preferably less than about 3% (by weight) azithromycin dihydrate, and most preferably less than 1% (by weight) azithromycin dihydrate.

As used herein, unless otherwise indicated, the term "bacterial infection(s)" or "protozoa infection" includes bacterial infections and protozoa infections and diseases caused by such infections that occur in mammals, fish and birds as well as disorders related to bacterial infections and protozoa infections that may be treated or prevented by administering antibiotics such as the compound of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*,or *Peptostreptococcus* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C. streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Also included are atherosclerosis and malaria. Bacterial infections and protozoa infections and disorders related to such infections that may be treated or prevented in animals include, but are not limited to, the following: bovine respiratory disease related to infection by *P. haem., P. multocida, Mycoplasma bovis*, or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius, coagulase neg. Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other bacterial infections and protozoa infections and disorders related to such infections that may be treated or prevented in accord with the method of the present invention are referred to in J. P. Sanford et al., "The Sanford Guide To Antimicrobial Therapy, " 26th Edition, (Antimicrobial Therapy, Inc., 1996).

The present invention also includes isotopically-labeled compounds wherein one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, and $^{17}O$. Such radiolabelled and stable-isotopically labelled compounds are useful as research or diagnostic tools.

DETAILED DESCRIPTION OF THE INVENTION

Figure 1:
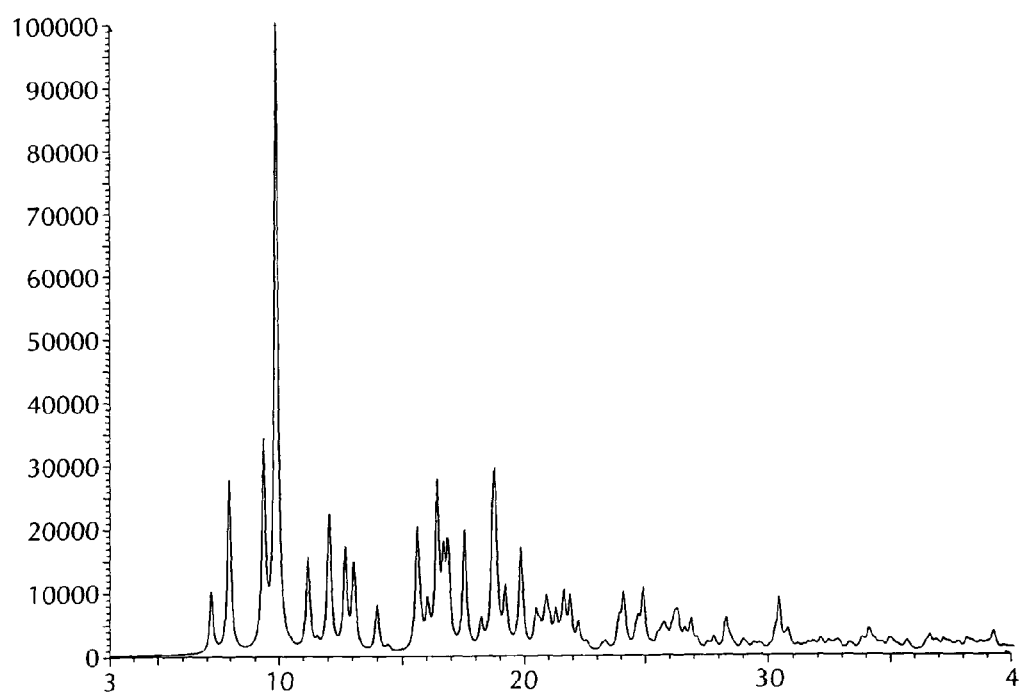
FIG. 1 is a calculated powder X-ray diffraction pattern of azithromycin form A. The scale of the abscissa is degrees 2-theta (2θ). The ordinate is the intensity in counts.

Azithromycin has been found to exist in different crystalline forms. A dihydrate, form A, and a non-stroichiometric hydrate, form B, are disclosed in European Patent EP 298 650 and U.S. Pat. No. 4,512,359, respectively. Sixteen other forms have been discovered, namely forms C, D, E, F, G, H, I, J, K, L, M, N, O, P, Q and R. These forms are either hydrates or hydrate/solvates of azithromycin free base. Forms L and K are the metastable lower hydrate forms of A, detected at high temperature. Crystal structures of forms A, C, D, E, F, G, H, J and O have been solved. The structural data of these crystal forms are given below:

TABLE 1

Crystallographic data of azithromycin form A.

| | Form A |
|---|---|
| Empirical formula | $C_{38}H_{72}N_2O_{12} \cdot 2H_2O$ |
| Formula weight | 785.2 |
| Crystal size (mm) | 0.19 × 0.24 × 0.36 |
| Space group | $P2_12_12_1$ orthorhombic |
| Unit cell dimensions | a = 14.735 (5) Å |
| | b = 16.844 (7) Å |
| | c = 17.81 (1) Å |
| | α = 90° |
| | β = 90° |
| | γ = 90° |
| Z (per formula) | 4 |
| Density (g/cm$^3$) | 1.18 |
| R | 0.060 |

TABLE 2

Crystallographic data of azithromycin form C.

| | Form C |
|---|---|
| Empirical formula | $C_{38}H_{72}N_2O_{12} \cdot H_2O$ |
| Formula weight | 767.15 |
| Crystal size (mm) | 0.16 × 0.16 × 0.19 |
| Space group | $P2_12_12_1$ orthorhombic |
| Unit cell dimensions | a = 8.809 (3) Å |
| | b = 12.4750 (8) Å |
| | c = 45.59 (3) Å |
| | α = 90° |

TABLE 2-continued

Crystallographic data of azithromycin form C.

| | Form C |
|---|---|
| | $\beta = 90°$ |
| | $\gamma = 90°$ |
| Z (per formula) | 4 |
| Density (g/cm$^3$) | 1.01 |
| R | 0.106 |

TABLE 3

Crystallographic data of azithromycin form D.

| | Form D |
|---|---|
| Empirical formula | $C_{38}H_{72}N_2O_{12} \cdot H_2O \cdot C_6H_{12}$ |
| Formula weight | 851.15 |
| Crystal size (mm) | 0.52 × 0.32 × 0.16 |
| Space group | $P2_12_12_1$ orthorhombic |
| Unit cell dimensions | a = 8.8710 (10) Å |
| | b = 12.506 (2) Å |
| | c = 45.697 (7) Å |
| | $\alpha = 90°$ |
| | $\beta = 90°$ |
| | $\gamma = 90°$ |
| Z (per formula) | 4 |
| Density (g/cm$^3$) | 1.12 |
| R | 0.0663 |

TABLE 4

Crystallographic data of azithromycin form E.

| | Form E |
|---|---|
| Empirical formula | $C_{38}H_{72}N_2O_{12} \cdot H_2O \cdot C_4H_8O$ |
| Formula weight | 839.2 |
| Crystal size (mm) | 0.17 × 0.19 × 0.20 |
| Space group | $P2_12_12_1$ orthorhombic |
| Unit cell dimensions | a = 8.869 (3) Å |
| | b = 12.086 (3) Å |
| | c = 46.00 (1) Å |
| | $\alpha = 90°$ |
| | $\beta = 90°$ |
| | $\gamma = 90°$ |
| Z (per formula) | 4 |
| Density (g/cm$^3$) | 1.13 |
| R | 0.087 |

TABLE 5

Crystallographic data of azithromycin form F.

| | Form F |
|---|---|
| Empirical formula | $C_{38}H_{72}N_2O_{12} \cdot H_2O \cdot 0.5C_2H_6O$ |
| Crystal size (mm) | 0.14 × 0.20 × 0.24 |
| Formula weight | 790.2 |
| Space group | $P2_1$ monoclinic |
| Unit cell dimensions | a = 16.281 (2) Å |
| | b = 16.293 (1) Å |
| | c = 18.490 (3) Å |
| | $\alpha = 90°$ |
| | $\beta = 109.33 (1)°$ |
| | $\gamma = 90°$ |
| Z (per formula) | 4 |
| Density (g/cm$^3$) | 1.13 |
| R | 0.0688 |

TABLE 6

Crystallographic data of azithromycin form G.

| | Form G |
|---|---|
| Formula | $C_{38}H_{72}N_2O_{12} \cdot 1.5H_2O$ |
| Formula weight | 776.0 |
| Crystal size (mm) | 0.04 × 0.20 × 0.24 |
| Space group | $P2_1$ monoclinic |
| Unit cell dimensions | a = 16.4069 (8) Å |
| | b = 16.2922 (8) Å |
| | c = 18.3830 (9) Å |
| | $\alpha = 90°$ |
| | $\beta = 110.212 (2)°$ |
| | $\gamma = 90°$ |
| Z (per formula) | 4 |
| Density (g/cm$^3$) | 1.12 |
| R | 0.0785 |

TABLE 7

Crystallographic data of azithromycin form H.

| | Form H |
|---|---|
| Empirical formula | $C_{38}H_{72}N_2O_{12} \cdot H_2O \cdot 0.5C_3H_8O_2$ |
| Crystal size (mm) | 0.14 × 0.20 × 0.24 |
| Formula weight | 805.0 |
| Space group | $P2_1$ monoclinic |
| Unit cell dimensions | a = 16.177 (1) Å |
| | b = 16.241 (2) Å |
| | c = 18.614 (1) Å |
| | $\alpha = 90°$ |
| | $\beta = 108.34 (1)°$ |
| | $\gamma = 90°$ |
| Z (per formula) | 4 |
| Density (g/cm$^3$) | 1.15 |
| R | 0.0687 |

TABLE 8

Crystallographic data of azithromycin form J.

| | Form J |
|---|---|
| Formula | $C_{38}H_{72}N_2O_{12} \cdot H_2O \cdot 0.5C_3H_8O$ |
| Formula weight | 796.0 |
| Crystal size (mm) | 0.40 × 0.36 × 0.20 |
| Space group | $P2_1$ monoclinic |
| Unit cell dimensions | a = 16.191 (6) Å |
| | b = 16.237 (10) Å |
| | c = 18.595 (14) Å |
| | $\alpha = 90°$ |
| | $\beta = 108.92 (4)°$ |
| | $\gamma = 90°$ |
| Z (per formula) | 4 |
| Density (g/cm$^3$) | 1.14 |
| R | 0.0789 |

TABLE 8A

Crystallographic data of azithromycin form O.

| | Form O |
|---|---|
| Formula | $C_{38}H_{72}N_2O_{12} \cdot 0.5H_2O \cdot 0.5C_4H_{10}O$ |
| Formula weight | 795.04 |
| Crystal size (mm) | 0.40 × 0.36 × 0.20 |
| Space group | $P2_1$ monoclinic |
| Unit cell dimensions | a = 16.3602 (11) Å |
| | b = 16.2042 (11) Å |
| | c = 18.5459 (12) Å |
| | $\alpha = 90°$ |

TABLE 8A-continued

Crystallographic data of azithromycin form O.

| | Form O |
|---|---|
| | β = 109.66 (10)° |
| | γ = 90° |
| Z (per formula) | 4 |
| Density (g/cm$^3$) | 1.14 |
| R | 0.0421 |

Among these sixteen crystal forms, two isomorphic families are identified. Family I includes forms F, G, H, J, M, N, O, and P. Family II includes forms C, D, E and R. Form Q is distinct from families I and II. The forms within a family are isomorphs that crystallize in the same space group with slight variation of cell parameters and comprise chemically related structures but different elemental composition. In this case, the variation in chemical composition among the isomorphs arises from incorporation of different water/solvent molecules. Consequently, the isomorphs display similar but non-identical X-ray diffraction patterns and solid-state NMR spectra (ssNMR). Other techniques such as near infrared spectroscopy (NIR), differential scanning calorimetry (DSC), gas chromatography (GC), thermalgravimetric analysis (TGA), or thermalgravimetric analysis/infrared spectroscopy analysis (TG-IR), Karl Fischer water analysis (KF) and molecular modeling/visualization provide data for affirmative identification of isomorphs. Dehydration/desolvation temperatures were determined by DSC with a heating rate of 5° C./min Form C: This crystal form was identified from a single crystal structure (Table 2)—a monohydrate of azithromycin. It has the space group of P2$_1$2$_1$2$_1$ and similar cell parameters as that of forms D and E; therefore, it belongs to Family II isomorphs. Its calculated powder pattern is similar to that of forms D and E.

Form D: Form D was crystallized from cyclohexane. The single crystal structure of form D shows a stoichiometry of a monohydrate/monocyclohexane solvate of azithromycin (Table 3). Cyclohexane molecules were found to be disordered in the crystal lattice. From single crystal data, the calculated water and cyclohexane content of form D is 2.1 and 9.9%, respectively. Both the powder pattern and the calculated powder pattern of form D are similar to those of forms C and E. The powder samples of form D showed a desolvation/dehydration endotherm with an onset temperature of about 87° C. and a broad endotherm between 200–280° C. (decomposition) in DSC analysis at 5° C./min from 30–300° C.

Form D is prepared by slurrying azithromycin in cyclohexane for 2–4 days. The solid form D azithromycin is collected by filtration and dried.

Form E: Form E was obtained as a single crystal collected in a THF/water medium. It is a monohydrate and mono-THF solvate by single crystal analysis (Table 4). By its single crystal structure, the calculated PXRD pattern is similar to that of form C and form D making it a family II isomorph.

Form E is prepared by dissolving azithromycin in THF (tetrahydrofuran). Diffusing water vapor through saturated azithromycin THF solution over time yields crystals of Form E.

Form F: The single crystal of form F crystallized in a monoclinic space group, P2$_1$, with the asymmetric unit containing two azithromycin, two waters, and one ethanol, as a monohydrate/hemi-ethanolate (Table 5). It is isomorphic to all family I azithromycin crystalline forms. The calculated PXRD pattern of this form is similar to those of other family I isomorphs. The theoretical water and ethanol contents are 2.3 and 2.9%, respectively. The powder samples show a dehydration/desolvation endotherm at an onset temperature between 110–125° C. Form F is prepared by dissolving azithromycin in ethanol (1–3 volumes by weight) at a temperature of about 50–70° C. Upon complete dissolution, the solution is cooled to subambient temperature to cause precipitation. The volume of ethanol can be reduced by vacuum distillation with stirring for 1–2 hours to increase the yield. Alternatively, water (optionally chilled to 0–20° C.) about 0.1–2 volume can be added with collection of solids within 30 minute after water addition. Cooling the ethanol solution of azithromycin prior to the addition of water to below below 20° C., preferably below 15° C., more preferably below 10, and most preferably 5° C. results in substantially pure azithromycin form F. The solid form F azithromycin is collected by filtration and dried.

Form G: The single crystal structure of form G consists of two azithromycin molecules and three water molecules per asymmetric unit (Table 6). This corresponds to a sesquihydrate with a theoretical water content of 3.5%. The water content of powder samples of form G ranges from about 2.5 to about 6%. The total residual organic solvent is less than 1% of the corresponding solvent used for crystallization, which is well below stoichiometric quantities of solvate. This form dehydrates with an onset temperature of about 110–120° C.

Form G may be prepared by adding azithromycin to a premixed organic solvent/water mixture (1/1 by volume), where the organic solvent can be methanol, acetone, acetonitrile, ethanol or isopropanol. The mixture is stirred and heated to an elevated temperature, e.g. 45–55° C. for 4–6 hours to cause dissolution. Precipitation occurs during cooling to ambient temperature. The solid form G azithromycin is collected by filtration and dried.

Form H: This crystal form is a monohydrate/hemi-propylene glycol solvate of azithromycin free base (Table 7). It was isolated from a formulation solution containing propylene glycol. The crystal structure of form H is isomorphic to crystal forms of Family I.

Azithromycin form H is prepared by dissolving azithromycin dihydrate in 6 volumes of propylene glycol. To the resulting propylene glycol solution of azithromycin, 2 volumes of water is added and precipitation occurrs. The slurry is stirred for 24 hours and the solids are filtered and air-dried at ambient temperature to afford crystalline Form H.

Form J: Form J is a monohydrate/hemi n-propanol solvate (Table 8). The calculated solvent content is about 3.8% n-propanol and about 2.3% water. The experimental data shows from about 2.5 to about 4.0% n-propanol and from about 2.5 to about 3% water content for powder samples. Its PXRD pattern is very similar to those of its isomorphs F, G, H, M and N. Like F and G, the powder samples have a dehydration/desolvation endotherm at 115–125° C.

Form J is prepared by dissolving azithromycin in 4 volumes of n-propanol at a temperature of about 25–55° C. Water, about 6–7 volumes, is added at room temperature and the slurry is continuously stirred for 0.5–2 hours. The solid form J azithromycin is collected by filtration and dried.

Form K: The PXRD pattern of form K was found in a mixture of azithromycin form A and microcrystalline wax after annealing at 95° C. for 3 hours. It is a lower hydrate of form A and is a metastable high temperature form.

Form L: This form has only been observed upon heating the dihydrate; form A. In variable temperature powder X-ray diffraction (VT-PXRD) experiments, a new powder X-ray diffraction pattern appears when form A is heated to about 90° C. The new form, designated form L, is a lower hydrate of form A because form A loses about 2.5 weight % at 90° C. by TGA, thus corresponding to a conversion to a monohydrate. When cooled to ambient temperature, form L rapidly reverts to form A.

Form M: Isolated from an isopropanol/water slurry, form M incorporates both water and isopropanol. Its PXRD pattern and ss-NMR spectrum are very similar to those of Family I isomorphs, indicating that it belongs to Family I. By analogy to the known crystal structures of Family I isomorphs, the single crystal structure of form M would be a monohydrate/hemi-isopropranolate. The dehydration/desolvation temperature of form M is about 115–125° C.

Form M may be prepared by dissolving azithromycin in 2–3 volumes of isopropanol (IPA) at 40–50° C. The solution is cooled to below 15° C., preferably below 10° C., more preferably about 5° C. and 2–4 volumes of cold water about 5° C. are added to effect precipitation. Seeds of form M crystals may be added at the onset of crystallization. The slurry is stirred less than about 5 hours, preferably less than about 3 hours, more preferably less than about 1 hour and most preferably about 30 minutes or less and the solids are collected by filtration. The solids may be reslurried in isopropanol. This procedure provides form M substantially in the absence of azithromycin dihydrate.

Form N: Isolated from water/ethanol/isopropanol slurry of form A, form N crystals may contain variable amounts of the crystallization solvents and water. Its water content varies from about 3.4 to about 5.3 weight percent. Analysis by GC Headspace reveals a variable solvent content of ethanol and isopropanol. The total solvent content of form N samples is usually lower than about 5% depending on the conditions of preparation and drying. The PXRD pattern of form N is similar to that of forms F, G, H, J and M of the Family I isomorphs. The dehydration/desolvation endotherm(s) of the samples of form N may be broader and may vary between 110–130° C.

Form N azithromycin may be prepared by recrystallizing azithromycin from a mixture of azithromycin crystal latice-incorporating organic solvents and water, such as ethanol, isopropanol, n-propanol, acetone, acetonitirile etc. The solvent mixture is heated to 45–60° C. and azithromycin is added to the heated solvent mixture, up to a total of about 4 volumes. Upon dissolution, 1–3 volumes of water are added with continuous agitation at 45–60° C. Form N azithromycin precipitates as a white solid. The slurry is allowed to cool to ambient temperature with stirring. Solid form N azithromycin is isolated by filtration and dried.

Form O: This crystal form is a hemihydrate hemi-n-butanol solvate of azithromycin free base by single crystal structural data (Table 8A). It was isolated from n-butanol solution of azithromycin with diffusion of antisolvent. The crystal structure of form O is isomorphic to crystal forms of Family I.

Azithromycin is completely dissolved in n-butanol. Addition of an antisolvent, such as hexane, water, IPE or other non-solvent, by diffusion results in precipitation of Form O.

Form P: This is a proposed crystal form, being a hemihydrate hemi-n-pentanol solvate of azithromycin free base. It can be isolated from an n-pentanol solution of azithromycin with diffusion of an antisolvent. The crystal structure of form P is isomorphic to crystal forms of Family I.

Form P of azithromycin may be prepared as following: Azithromycin is completely dissolved in n-pentanol; addition of an antisolvent, such as hexane, water, isopropyl ether (IPE) or other non-solvent, by diffusion results in precipitation of Form P.

Form Q: The crystal form of Q exhibits a unique powder X-ray diffraction pattern. It contains about 4% water and about 4.5% THF, being a hydrate hemi THF solvate. The main dehydration/desolvation temperature is from about 80 to about 110° C.

Azithromycin dihydrate is dissolved in 6 volumes of THF and 2 volumes of water are added. The solution is allowed to evaporate to dryness at ambient conditions to afford crystalline Form Q.

Form R: This crystalline form is prepared by adding amorphous azithromycin to 2.5 volumes of tert-butyl methyl ether (MTBE). The resulting thick white suspension is stirred 3 days at ambient conditions. Solids are collected by vacuum filtration and air dried. The resulting bulk azithromycin form R has a theoretical water content of 2.1 weight % and a theoretical methyl tert-butyl ether content of 10.3 weight %.

Due to the similarity in their structures, isomorphs have propensity to form a mixture of the forms within a family, sometimes termed as 'mixed crystals' or 'crystalline solid solution'. Form N is such a solid crystalline solution and was found to be a mixture of Family I isomorphs by solvent composition and solid-state NMR data.

Both Family I and Family II isomorphs are hydrates and/or solvates of azithromycin. The solvent molecules in the cavities have tendency to exchange between solvent and water under specific conditions. Therefore, the solvent/water content of the isomorphs may vary to a certain extent.

The crystal forms of isomorphic Family I are more stable than form A when subjected to heating. Forms F, G, H, J, M and N showed higher onset dehydration temperatures at 110–125° C. than that of form A with an onset dehydration temperature at about 90 to about 110° C. and simultaneous solid-state conversion to form L at about 90° C.

Amorphous azithromycin: All crystal forms of azithromycin contain water or solvent(s) or both water and solvent(s). When water and solvent(s) are removed from the crystalline solids, azithromycin becomes amorphous. Amorphous solids have advantages of high initial dissolution rates.

The starting material for the synthesis of the various crystal forms in the examples below was azithromycin dihydrate unless otherwise noted. Other forms of azithromycin such as amorphous azithromycin or other non-dihydrate crystalline forms of azithromycin may be used.

EXAMPLES

Example 1

Preparation of Form D

Form D was prepared by slurrying azithromycin dihydrate in cyclohexane for 2–4 days at an elevated temperature, e.g. 25–50° C. The crystalline solids of form D were collected by filtration and dried.

Example 2

Preparation of Form F

2A: Azithromycin dihydrate was slowly added to one volume of warm ethanol, about 70° C., and stirred to complete dissolution at 65 to 70° C. The solution was allowed to cool gradually to 2–5° C. and one volume of chilled water was added The crystalline solids were collected shortly (preferably less than 30 minutes) after addition of water by vacuum filtration.

2B: Azithromycin dihydrate is slowly added to one volume of warm ethanol, about 70° C., and stirred to complete dissolution at 65 to 70° C. The solution is allowed to cool gradually to 2–5° C. and ethanol volume may be reduced by vacuum distillation. Seeds of Form F 1–2% wt may be introduced to facilitate the crystallization. After stirring up to 2 hours the crystalline solids are collected by vacuum filtration. The isolation of the crystals yields substantially pure form F azithromycin, form F azithromycin substantially free of form G azithromycin and form F azithromycin substantially free of azithromycin dihydrate.

Example 3

Preparation of Form G

A reaction vessel was charged with form A azithromycin. In a separate vessel, 1.5 volumes methanol and 1.5 volumes water were mixed. The solvent mixture was added to the reaction vessel containing the form A azithromycin. The slurry was stirred with heating to 50° C. for approximately 5 hours. Heating was discontinued and the slurry was allowed to cool with stirring to ambient temperature. The form G azithromycin was collected by filtration and allowed to air dry for approximately 30 minutes. The collected form G azithromycin was further dried in a vacuum oven at 45° C. This procedure yields substantially pure form G azithromycin, and form G azithromycin substantially free of azithromycin dihydrate.

Example 4

Preparation of Form J

Form J was prepared by dissolving azithromycin in 4 volumes of n-propanol at a temperature of about 25° C. Water (6.7 volumes) was added and the slurry is continuously stirred for 1 hour, followed by cooling to about 0° C. The solid form J azithromycin was collected by filtration and dried.

Example 5

Preparation of Form M Substantially in the Absence of Azithromycin Dihydrate

5A: Azithromycin dihydrate is completely dissolved in 2 volumes of warm isopropanol 40–50° C. Seeds of Form M may be optionally introduced to facilitate the crystallization. The solution is then cooled to 0–5° C. and 4 volumes of chilled water as antisolvent are added and the solids are collected by vacuum filtration. The solids are reslurried in 1 volume of isopropanol for 3–5 hours at 40–45° C. and then cooled to 0–5° C. The crystalline solids are collected shortly (about 15 minutes) after addition of water by vacuum filtration. The solids are reslurried in 0.5 to 1 volume of isopropanol at 25–40° C. and cooled to about 5° C. followed by filtration to collect solids of form M.

These procedures yield substantially pure form M azithromycin, form M azithromycin substantially free of form G azithromycin and form M azithromycin substantially free of azithromycin dihydrate.

Example 6

Preparation of Form N

Two volumes of ethanol and 2 volumes of isopropanol were added to a reaction vessel and heated to 50° C. Azithromycin form A was added with stirring to the heated ethanol/isopropanol mixture to yield a clear solution. The reaction vessel was charged with 2 volumes distilled water (ambient temperature). Stirring was continued at 50° C. and solid form N azithromycin precipitated after approximately 1 hr. Heating was discontinued 5 hours after the addition of the water. The slurry was allowed to cool to ambient temperature. Precipitated form N azithromycin was collected by filtration and dried for 4 hours in vacuum oven at 45° C.

Example 7

Preparation of Amorphous Azithromycin

Crystalline form A azithromycin was heated to 110–120° C. in an oven for overnight under vacuum. The amorphous solids were collected and stored with desiccant as needed.

Example 8

Preparation of Form H

Azithromycin dihydrate or other crystal forms was dissolved in 6 volumes of propylene glycol. To the resulting propylene glycol solution of azithromycin, 2 volumes of water were added and precipitation occurred. The slurry was stirred for 24 hours and the solids were filtered and air-dried at ambient temperature to afford crystalline Form H.

Example 9

Preparation of Form Q

The crystalline powder was prepared by dissolving 500 mg azithromycin Form A in 2 ml THF. To the clear, colorless solution at room temperature was added 1 ml water. When the solution became cloudy an additional 1 ml THF was added to dissolve the azithromycin completely, and the solution was stirred at ambient temperature. Solvent was allowed to evaporate over 7 days, after which the dry solids were collected and characterized.

Example 10

Powder X-ray Diffraction Analysis

Powder patterns were collected using a Bruker D5000 diffractometer (Madison, Wis.) equipped with copper radiation, fixed slits (1.0, 1.0, 0.6 mm), and a Kevex solid state detector. Data was collected from 3.0 to 40.0 degrees in 2 theta using a step size of 0.04 degrees and a step time of 1.0 seconds. The results are summarized in Table 9.

Figure 2:
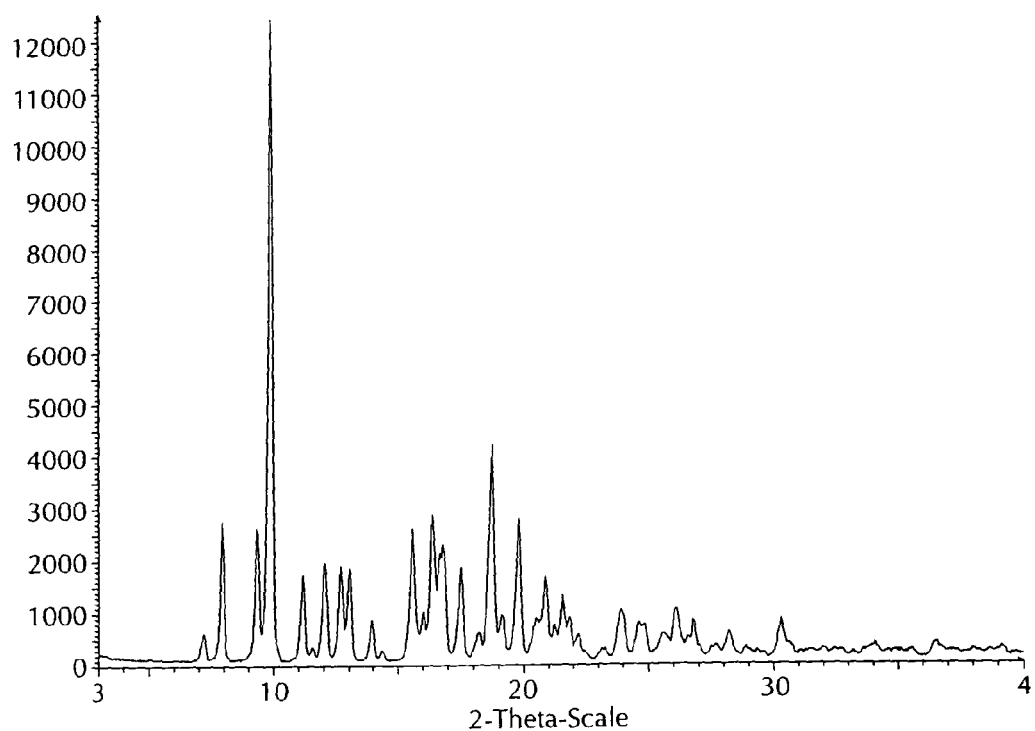
FIG. 2 is an experimental powder X-ray diffraction pattern of azithromycin form A. The scale of the abscissa is in degrees 2-theta (2θ). The ordinate is the intensity in counts.
Figure 3:
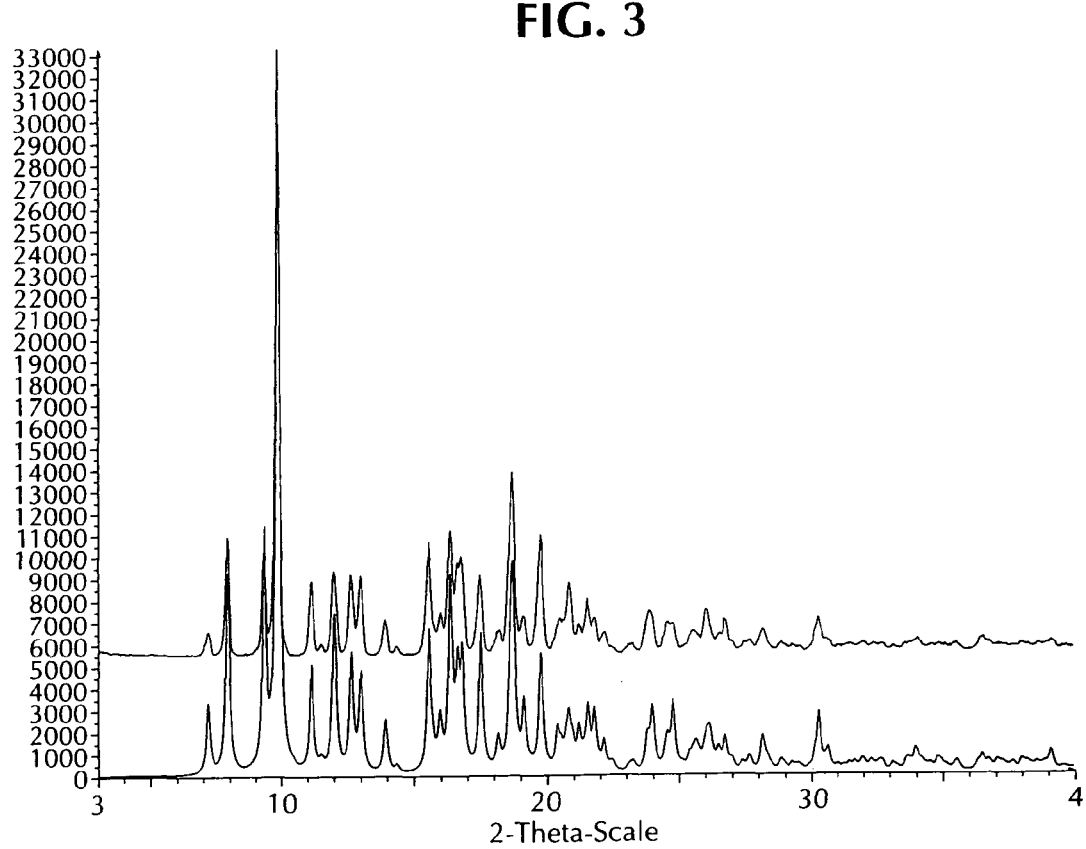
FIG. 3 is an overlay of FIGS. 1 and 2 with the calculated diffraction patterns of azithromycin form A (FIG. 1) on the bottom and the experimental diffraction pattern of azithromycin form A (FIG. 2) on the top. The scale of the abscissa is in degrees 2-theta (2θ). The ordinate is the intensity in counts.
Figure 4:
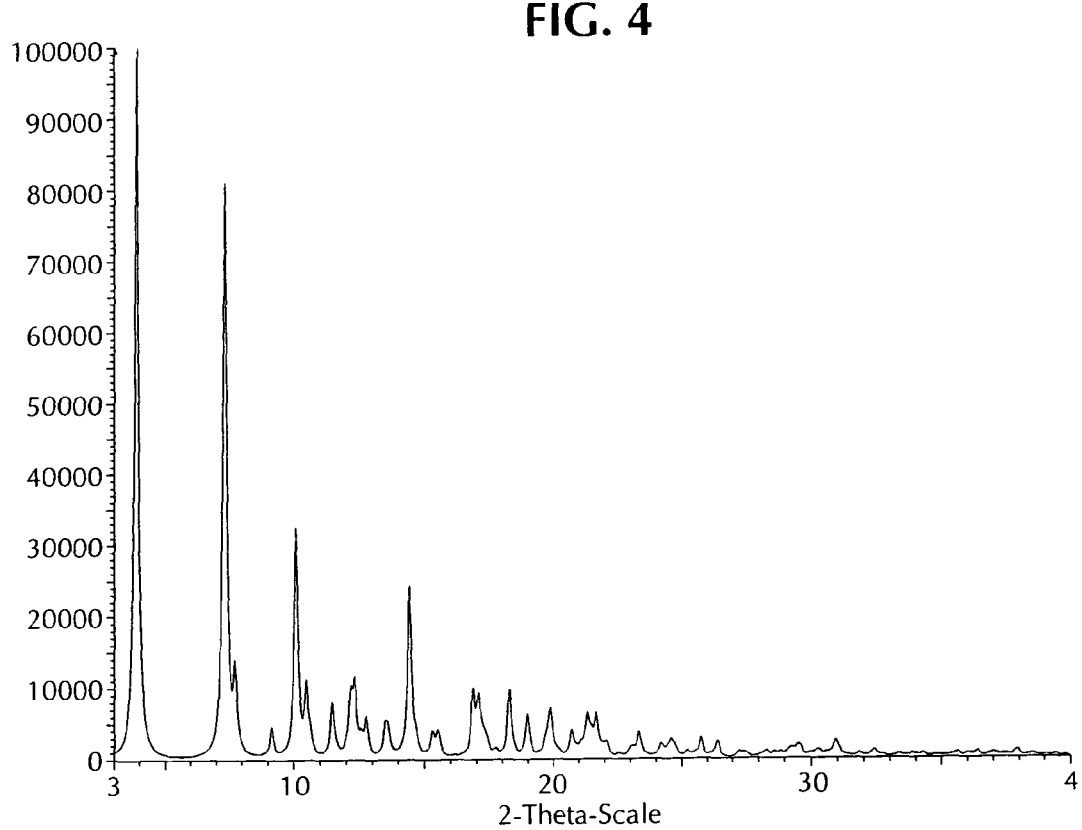
FIG. 4 is a calculated powder X-ray diffraction pattern of azithromycin form C. The scale of the abscissa is in degrees 2-theta (2θ). The ordinate is the intensity in counts.

The experimental PXRD diffraction pattern of azithromycin form A is given in FIG. 2.

Figure 6:
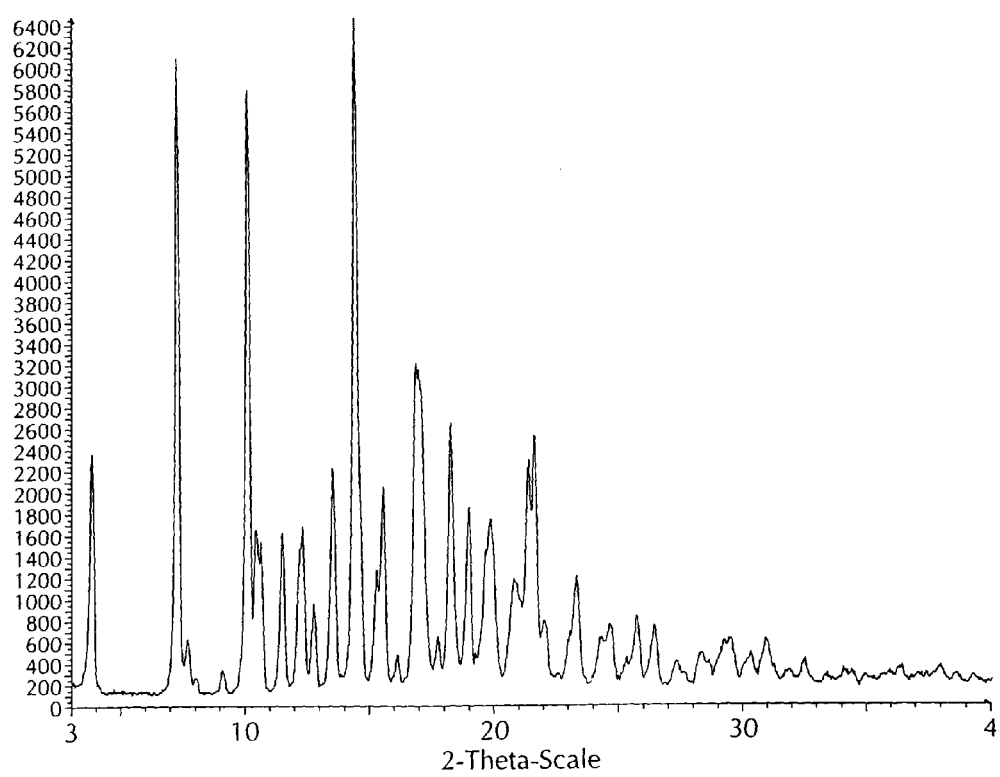
FIG. 6 is an experimental powder X-ray diffraction pattern of azithromycin form D. The scale of the abscissa is in degrees 2-theta (2θ). The ordinate is the intensity in counts.
Figure 7:
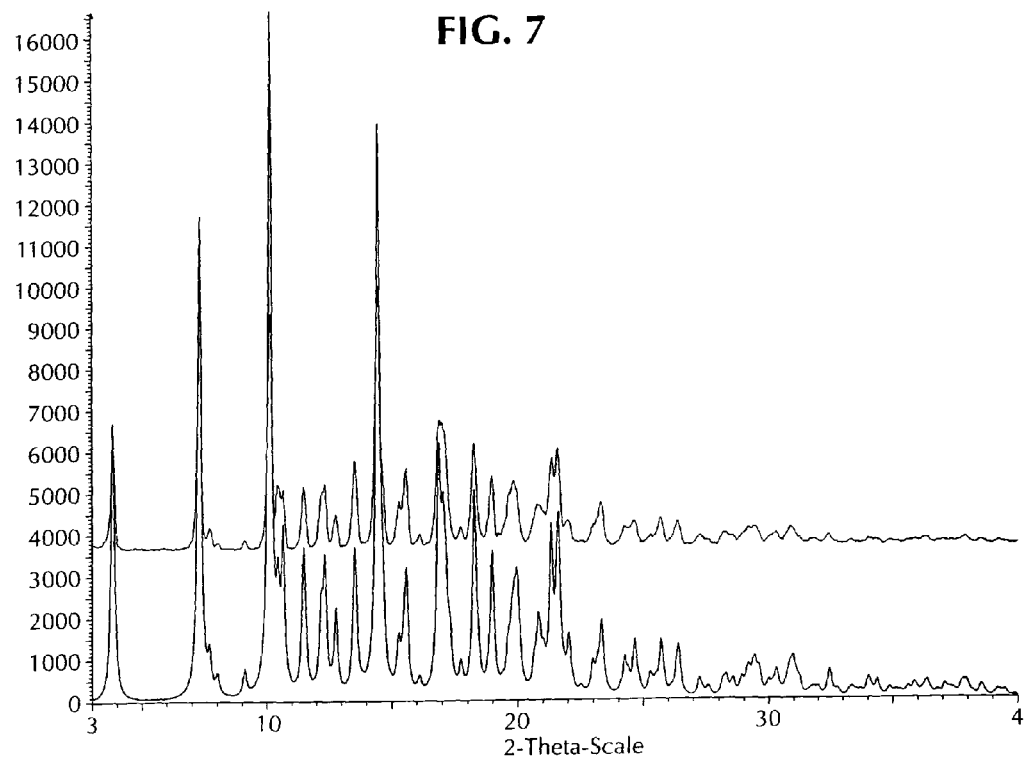
FIG. 7 is an overlay of FIGS. 5 and 6 with the calculated diffraction pattern of azithromycin form D (FIG. 5) on the bottom and the experimental diffraction pattern of azithromycin form D (FIG. 6) on the top. The scale of the abscissa is in degrees 2-theta (2θ). The ordinate is the intensity in counts.
Figure 8:
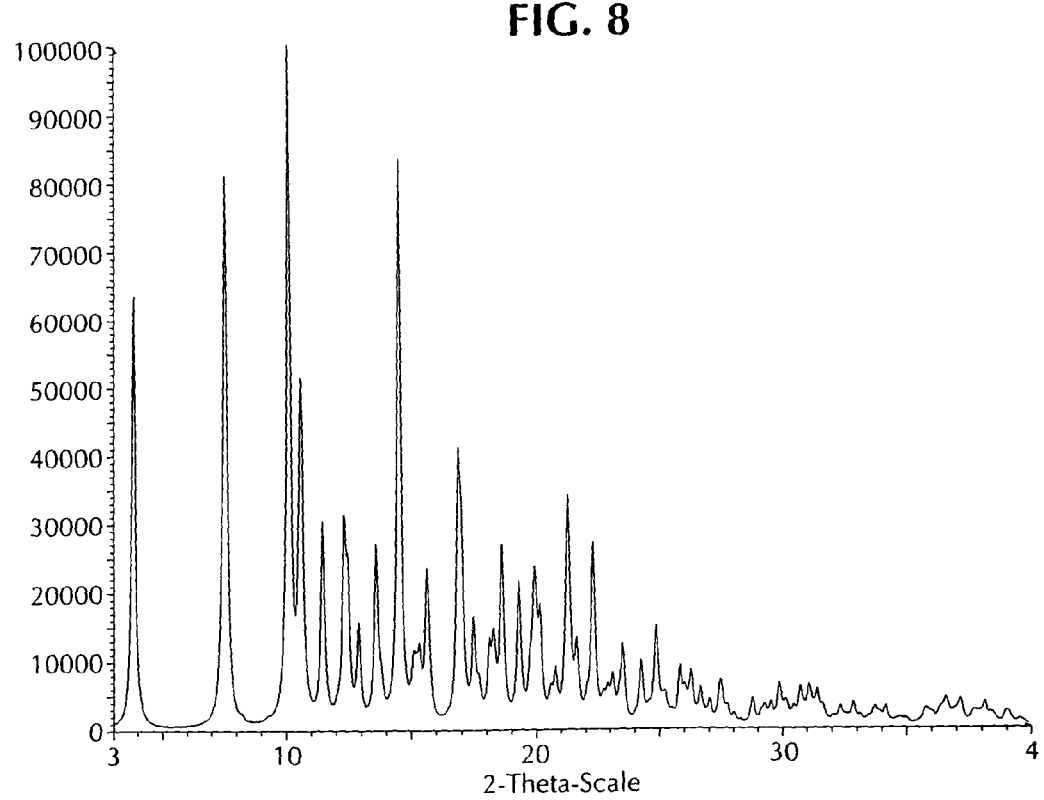
FIG. 8 is a calculated powder X-ray diffraction pattern of azithromycin form E. The scale of the abscissa is in degrees 2-theta (2θ). The ordinate is the intensity in counts.

The experimental PXRD diffraction pattern of azithromycin form D is given in FIG. 6.

Figure 10:
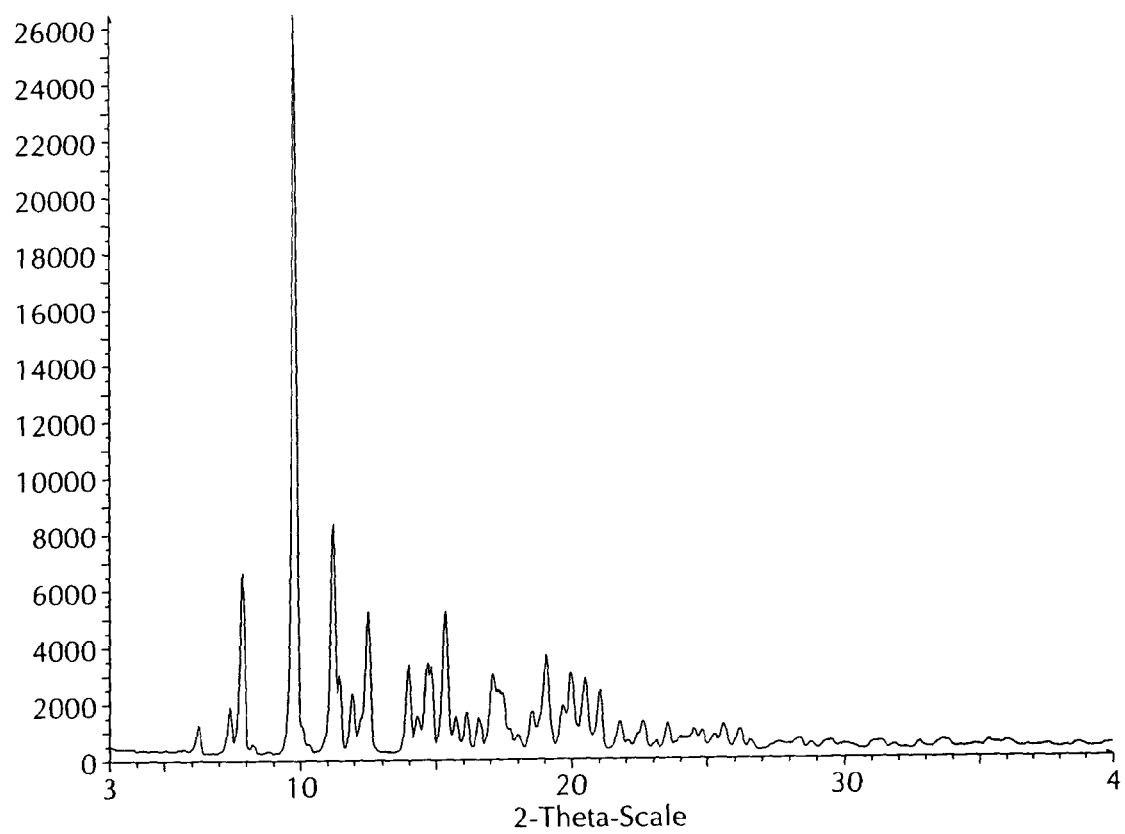
FIG. 10 is an experimental powder X-ray diffraction pattern of azithromycin form F. The scale of the abscissa is in degrees 2-theta (2θ). The ordinate is the intensity in counts.
Figure 11:
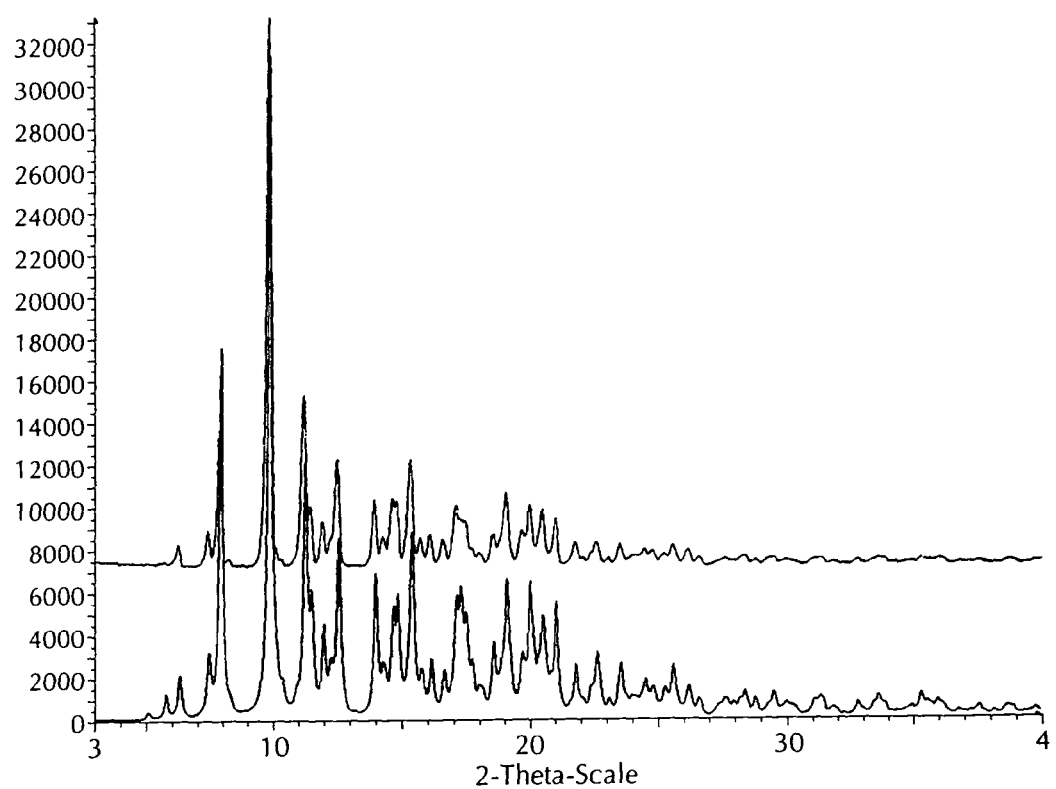
FIG. 11 is an overlay of FIGS. 9 and 10 with the calculated diffraction pattern of azithromycin form F (FIG. 9) on the bottom and the experimental diffraction pattern of azithromycin form F (FIG. 10) on the top. The scale of the abscissa is in degrees 2-theta (2θ). The ordinate is the intensity in counts.

The experimental PXRD diffraction pattern of azithromycin form F is given in FIG. 10.

Figure 13:
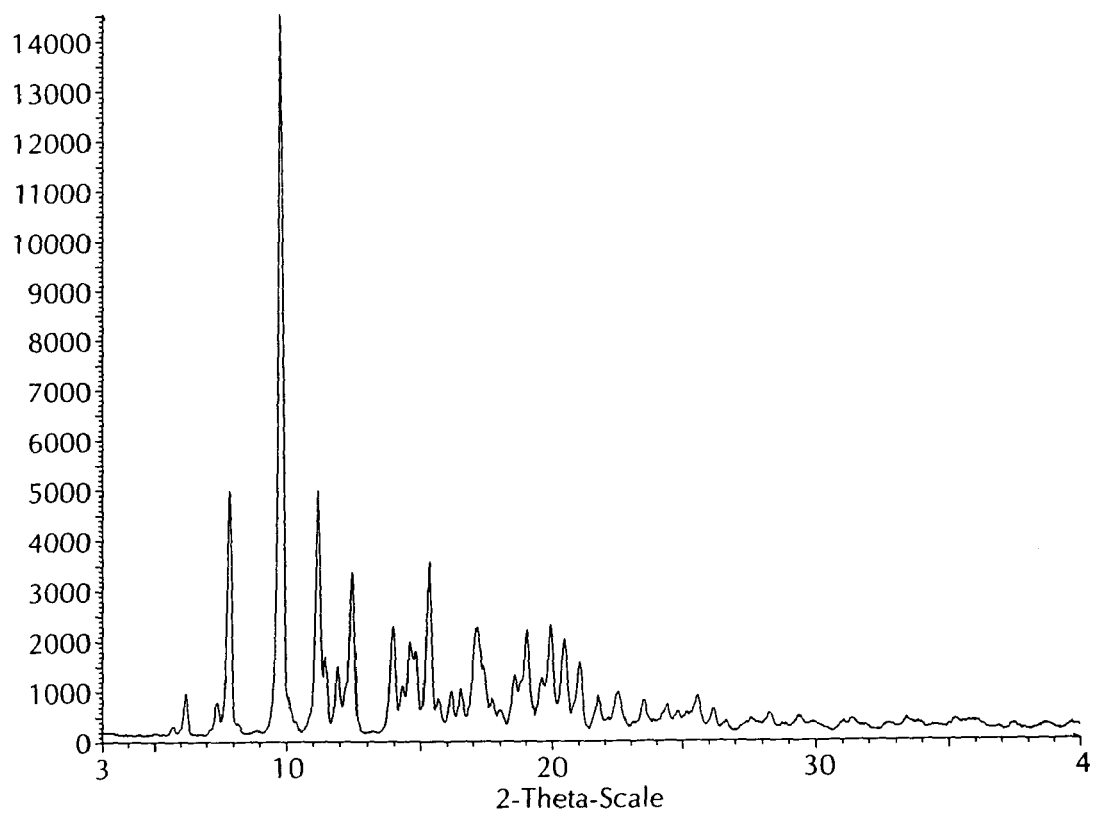
FIG. 13 is an experimental powder X-ray diffraction pattern of azithromycin form G. The scale of the abscissa is in degrees 2-theta (2θ). The ordinate is the intensity in counts.
Figure 14:
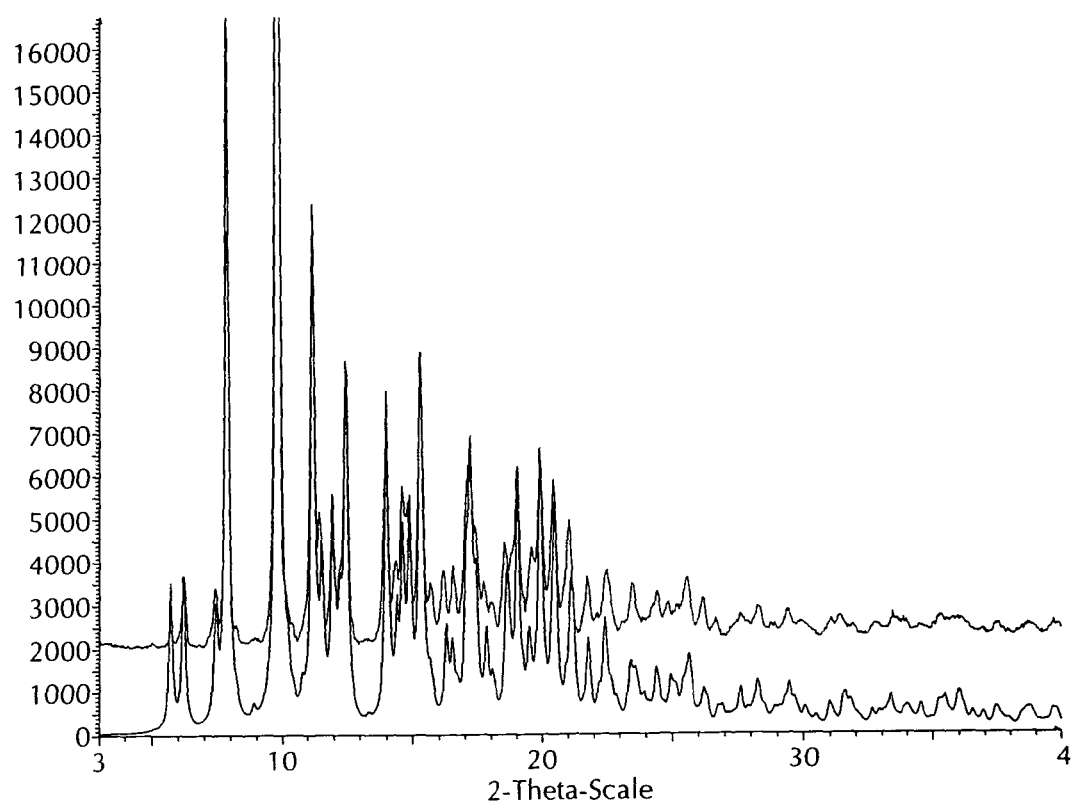
FIG. 14 is an overlay of FIGS. 12 and 13 with the calculated diffraction pattern of azithromycin form G (FIG. 12) on the bottom and the experimental diffraction pattern of azithromycin form G (FIG. 13) on the top. The scale of the abscissa is in degrees 2-theta (2θ). The ordinate is the intensity in counts.

The experimental PXRD diffraction pattern of azithromycin form G is given in FIG. 13.

Figure 16:
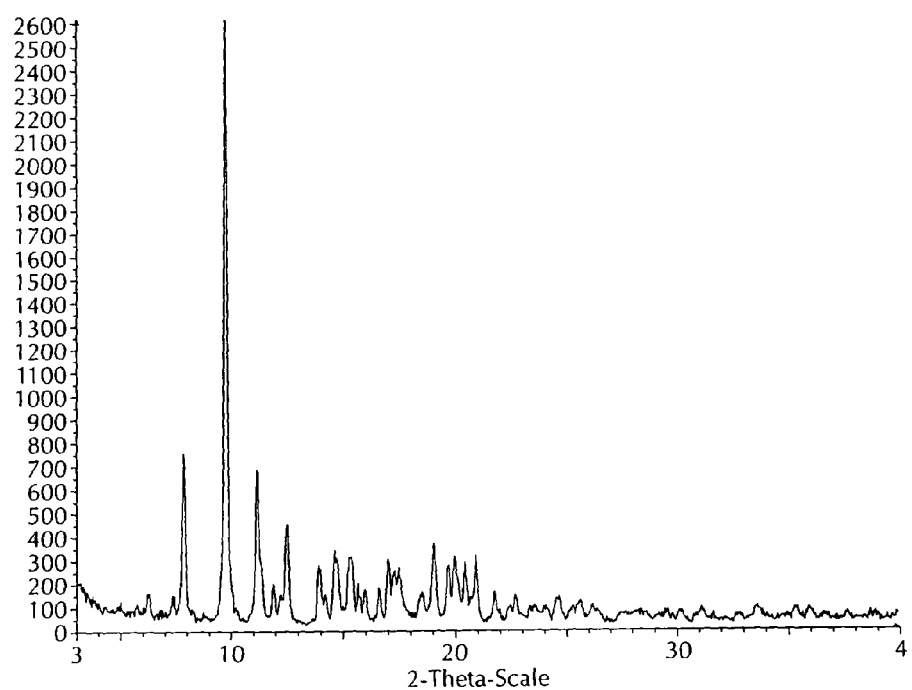
FIG. 16 is an experimental powder X-ray diffraction pattern of azithromycin form J. The scale of the abscissa is in degrees 2-theta (2θ). The ordinate is the intensity in counts.
Figure 17:
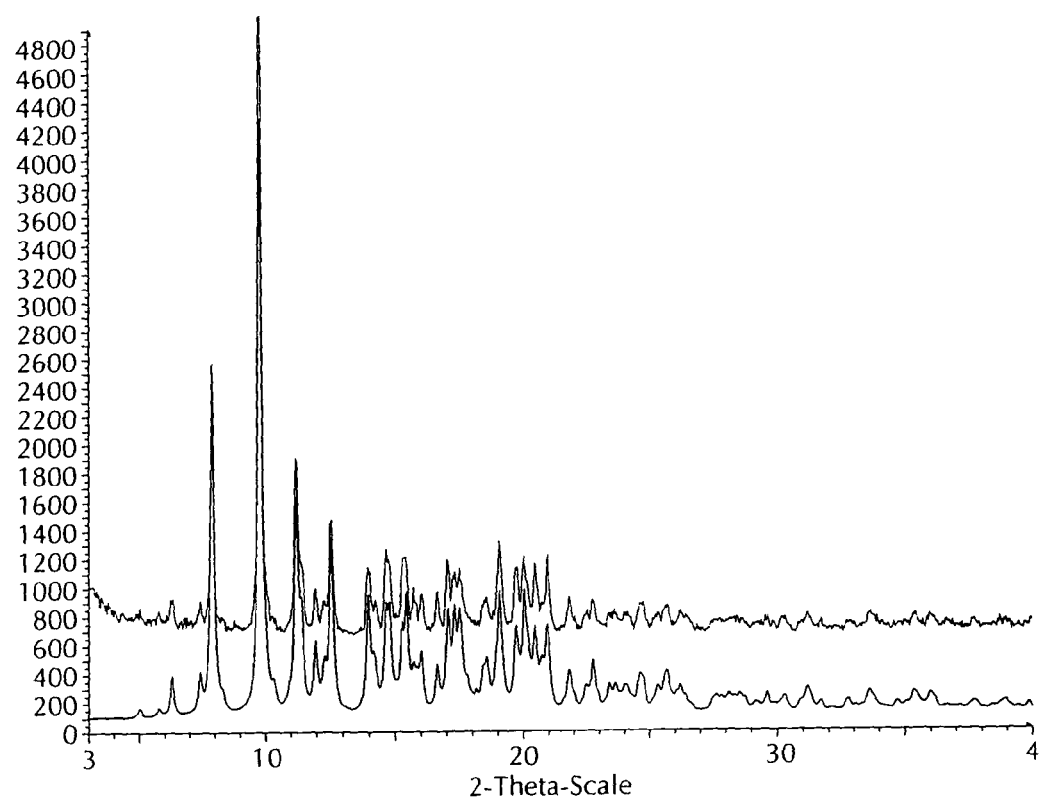
FIG. 17 is an overlay of FIGS. 15 and 16 with the calculated diffraction pattern of azithromycin form J (FIG. 15) on the bottom and the experimental diffraction pattern of azithromycin form J (FIG. 16) on the top. The scale of the abscissa is in degrees 2-theta (2θ). The ordinate is the intensity in counts.

The experimental PXRD diffraction pattern of azithromycin form J is given in FIG. 16.

Figure 18:
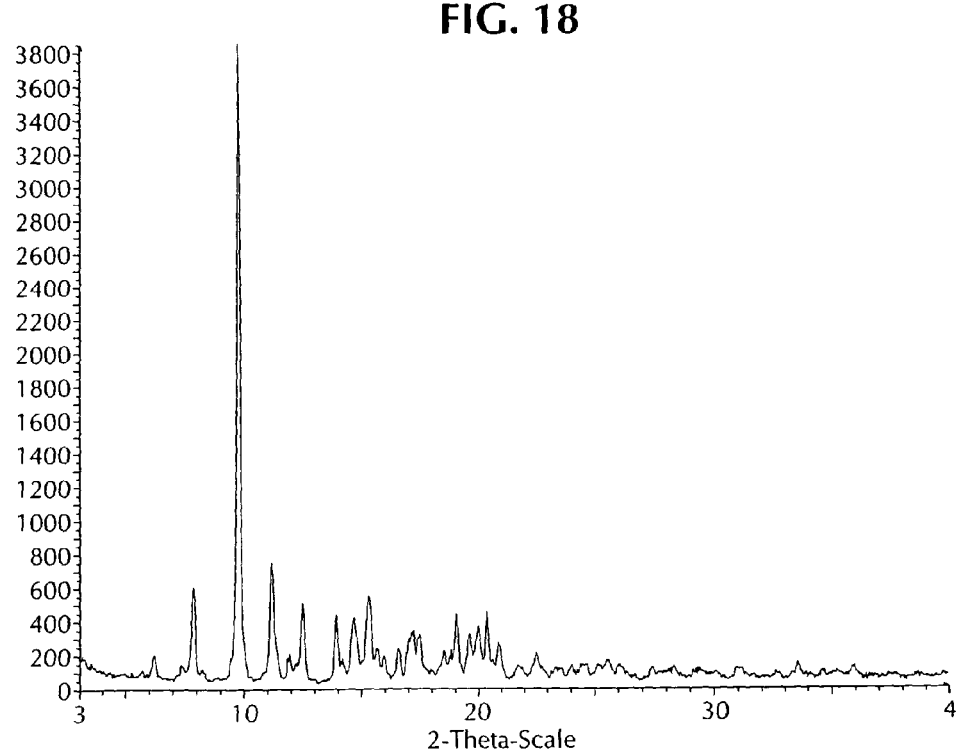
FIG. 18 is an experimental powder X-ray diffraction pattern of azithromycin form M. The scale of the abscissa is in degrees 2-theta (2θ). The ordinate is the intensity in counts.

The experimental PXRD diffraction pattern of azithromycin form M is given in FIG. 18.

Figure 19:
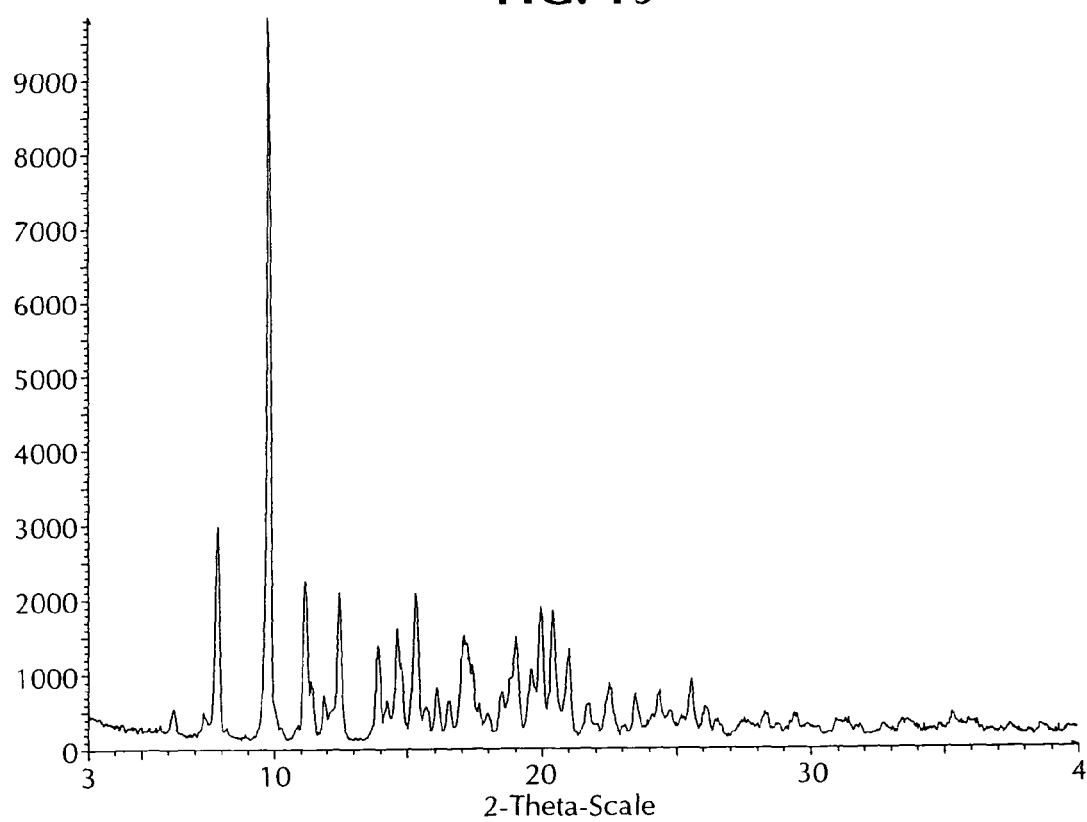
FIG. 19 is an experimental powder X-ray diffraction pattern of azithromycin form N. The scale of the abscissa is in degrees 2-theta (2θ). The ordinate is the intensity in counts.

The experimental PXRD diffraction pattern of azithromycin form N is given in FIG. 19.

Figure 20:
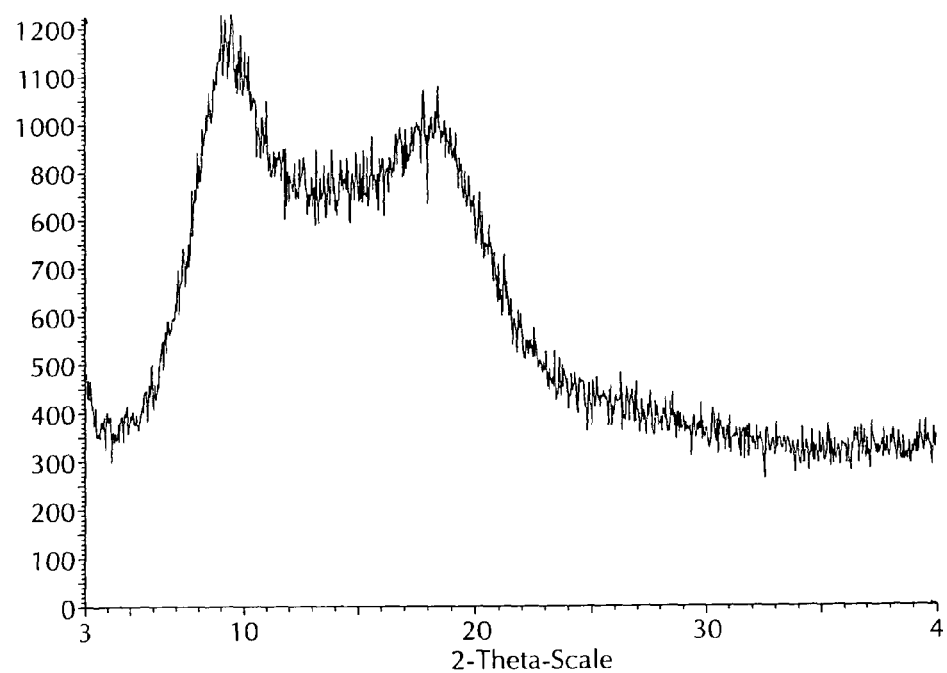
FIG. 20 is an experimental powder X-ray diffraction pattern of amorphous azithromycin. The scale of the abscissa is in degrees 2-theta (2θ). The ordinate is the intensity in counts.

The experimental PXRD diffraction pattern of amorphous azithromycin is given in FIG. 20.

Figure 30:
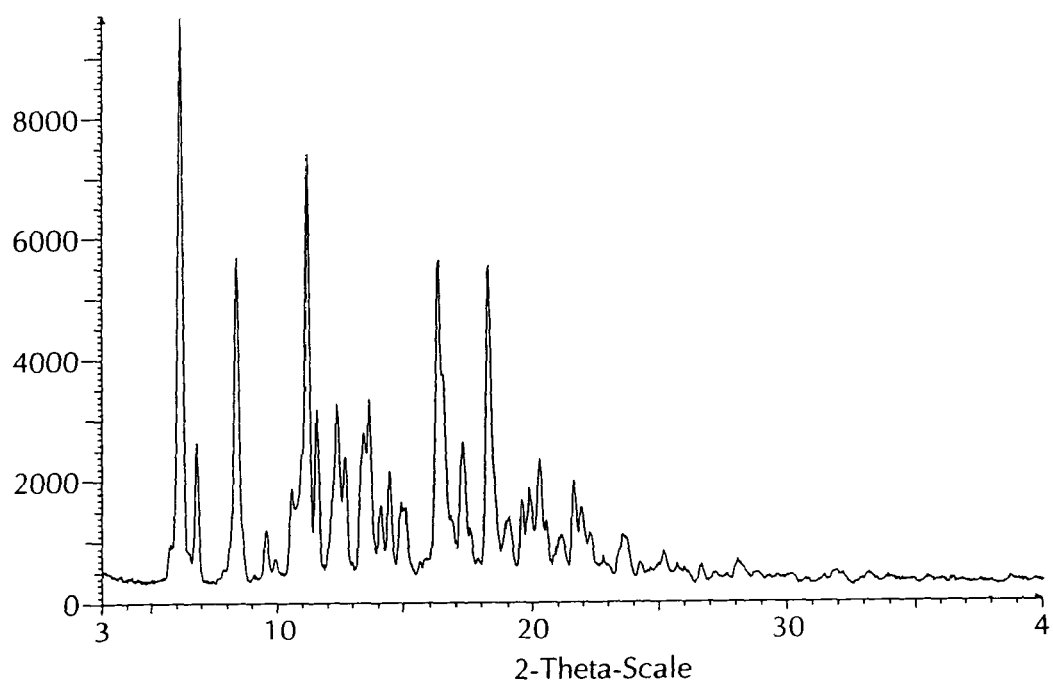
FIG. 30 is an experimental powder X-ray diffraction pattern of azithromycin form Q. The scale of the abscissa is in degrees 2-theta (2θ). The ordinate is the intensity in counts.

The experimental PXRD diffraction pattern of azithromycin form Q is given in FIG. 30.

Figure 31:
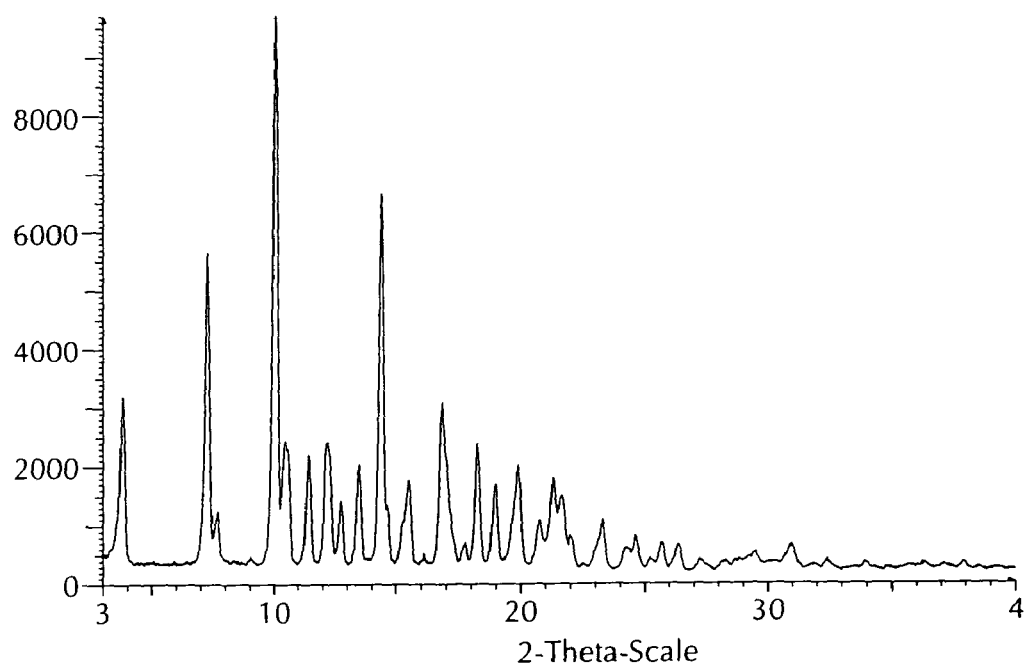
FIG. 31 is an experimental powder X-ray diffraction pattern of azithromycin form R. The scale of the abscissa is in degrees 2-theta (2θ). The ordinate is the intensity in counts.
Figure 32:
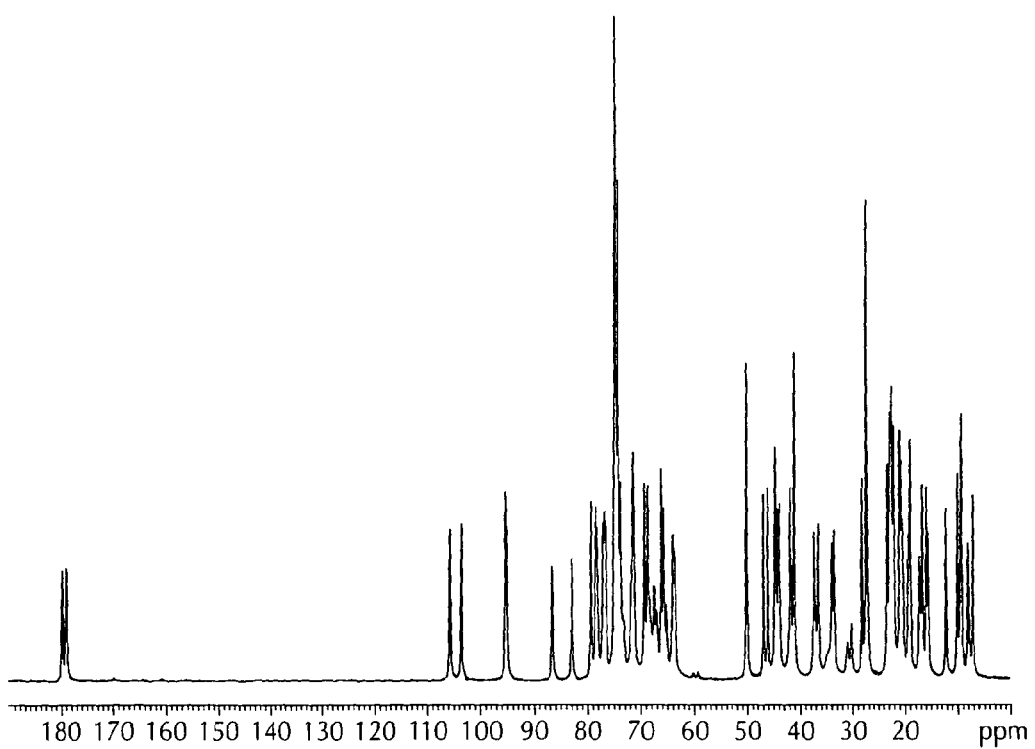
FIG. 32 is a $^{13}$C solid state NMR spectrum of azithromycin form H.
Figure 33:
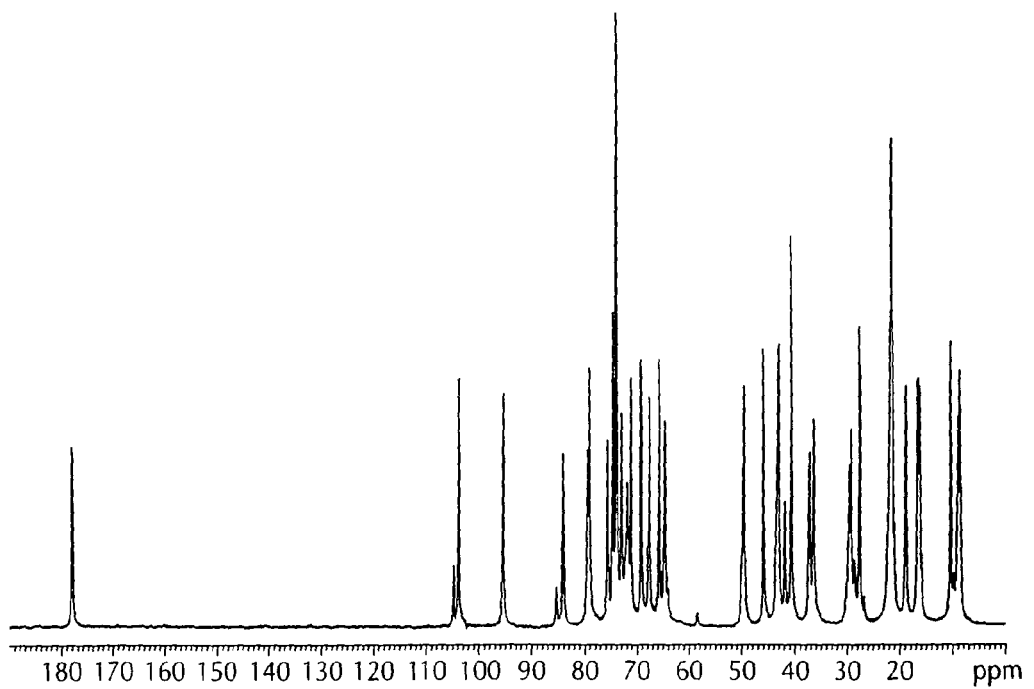
FIG. 33 is a $^{13}$C solid state NMR spectrum of azithromycin form R.

The experimental PXRD diffraction pattern of azithromycin form R is given in FIG. 31.

The experimental variability from sample to sample is about ±0.2° in 2 theta, and the same variations were observed between the calculated powder from single crystal structure and experimental data. Detailed analysis showed that the isomorphs in Family I can be discerned by PXRD with sets of characteristic peaks given in Table 9.

TABLE 9

Azithromycin Powder X-ray Diffraction Peaks in 2-theta ±0.2°

| A | D | F | G | J | M | N | Q |
|---|---|---|---|---|---|---|---|
| 7.2 | _3.9_ | 5.7 | 5.0 | 5.0 | 5.0 | _6.2_ | 5.7 |
| 7.9 | 7.3 | _6.2_ | 5.8 | 5.7 | 5.6 | 7.3 | 6.1 |
| _9.3_ | 7.7 | 7.4 | _6.2_ | _6.2_ | _6.2_ | 7.8 | _6.8_ |
| 9.9 | _10.1_ | 7.8 | 7.4 | 7.3 | 7.3 | 9.8 | _8.4_ |
| 11.2 | _10.6_ | 8.9 | 7.9 | 7.8 | 7.8 | _11.2_ | 9.5 |
| 12.0 | 11.5 | 9.8 | 9.8 | 8.2 | 8.2 | 11.9 | 10.6 |
| 12.7 | 12.3 | 10.3 | 10.2 | 9.7 | 9.8 | 12.5 | 11.2 |
| _13.0_ | 12.8 | _11.2_ | 10.8 | 10.3 | 10.2 | _14.0_ | 11.5 |
| 14.0 | 13.6 | _11.5_ | _11.2_ | _11.2_ | _11.2_ | _14.3_ | 12.4 |
| 15.6 | 14.5 | 11.9 | _11.6_ | _11.4_ | 11.9 | _14.7_ | 12.7 |
| 16.0 | 15.4 | 12.2 | 12.0 | 11.9 | 12.2 | 15.3 | 13.4 |
| 16.4 | 15.6 | 12.5 | 12.5 | 12.3 | 12.5 | 15.7 | 13.6 |
| 16.8 | 16.9 | _13.9_ | 13.3 | 12.5 | _14.0_ | _16.1_ | 14.1 |
| 17.5 | 18.3 | _14.3_ | _14.0_ | _13.9_ | _14.6_ | _16.6_ | 14.4 |
| 18.2 | 19.0 | _14.7_ | _14.4_ | _14.2_ | 15.3 | _17.1_ | 14.9 |
| _18.7_ | 19.9 | _14.8_ | _14.6_ | _14.6_ | _15.9_ | _17.4_ | 16.3 |
| 19.1 | 20.8 | 15.3 | _14.9_ | 15.3 | _16.6_ | 18.5 | 17.2 |
| 19.8 | _21.4_ | 15.7 | 15.3 | 15.7 | _17.1_ | 19.0 | 18.2 |
| 20.5 | 21.6 | _16.2_ | 15.7 | _16.0_ | _17.5_ | 19.6 | 19.0 |
| 20.9 | 22.0 | _16.6_ | _16.3_ | _16.6_ | 18.4 | 20.0 | 19.5 |
| 21.2 | 23.0 | _17.1_ | _16.6_ | _17.0_ | 18.5 | 20.4 | 19.8 |
| 21.6 | 23.3 | _17.2_ | _17.2_ | _17.2_ | 19.1 | _21.0_ | _20.2_ |
| 21.8 |  | _17.7_ | _17.4_ | _17.5_ | 19.6 | 21.8 | 20.5 |
| 24.0 |  | 18.0 | _17.8_ | 18.1 | 20.0 | _22.5_ | 21.1 |
|  |  | 18.5 | 18.1 | 18.5 | 20.4 | 23.5 | 21.6 |
|  |  | 19.0 | 18.6 | 19.0 | _20.9_ |  | 21.9 |
|  |  | 19.6 | 19.0 | 19.7 | 21.7 |  | 22.2 |
|  |  | 20.0 | 19.6 | 20.0 | _22.5_ |  | 23.6 |
|  |  | 20.5 | 20.0 | 20.4 | 23.2 |  | 25.1 |
|  |  | _21.0_ | 20.5 | _20.9_ | 23.6 |  |  |
|  |  | 21.7 | _21.1_ | 21.7 |  |  |  |
|  |  | 22.0 | 21.8 | 22.4 |  |  |  |
|  |  | _22.4_ | _22.5_ | _22.6_ |  |  |  |
|  |  | 22.6 | 23.5 | 23.3 |  |  |  |
|  |  | 23.1 |  | 23.5 |  |  |  |
|  |  | 23.5 |  |  |  |  |  |

The peaks underlined are the characteristic peaks among forms A, D, Family I and Q.

The peaks in italic and underlined are the sets of peaks that are characteristic within Family I isomorphs.

Family I isomorphs have the following common characteristics: the diffraction peaks at 6.2, 11.2, 21.0±0.1 and 22.5±0.1 degree in 2-theta. Each isomorph displays representative sets of diffraction peaks given in the following, and each set has characteristic spacing between the peaks.

The diffraction peak positions reported are accurate to within ±0.2 degree of 2-theta.

A representative PXRD pattern of form A is shown in FIG. 2. Form A displays peaks at 9.3, 13.0 and 18.7 degrees of 2-theta.

A representative PXRD pattern of form D is shown in FIG. 6. Form D displays peaks at 3.9, 10.1, 10.6 and 21.4 degrees of 2-theta.

A representative PXRD pattern of Form F is shown in FIG. 10. Form F displays the characteristic peaks of Family I and three sets of peaks, being set 1 at 2-theta of 11.2 and 11.5; set 2 at 2-theta of 13.9, 14.3, 14.7 and 14.8; set 3 at 2-theta of 16.2, 16.6, 17.1, 17.2 and 17.7.

A representative PXRD pattern of Form G is shown in FIG. 13. Form G displays the characteristic peaks of Family I and three sets of peaks, being set 1 at 2-theta of 11.2 and 11.6 2; set 2 at 2-theta of 14.0, 14.4, 14.6 and 14.9; set 3 at 2-theta of 16.3, 16.6, 17.2, 17.4 and 17.8.

A representative PXRD pattern of Form J is shown in FIG. 16. Form J displays the characteristic peaks of Family I and three sets of peaks, being set 1 at 2-theta of 11.2 and 11.4; set 2 at 2-theta of 13.9, 14.2 and 14.6; set 3 at 2-theta of 16.0, 16.6, 17.0, 17.2 and 17.5.

A representative PXRD pattern of Form M is shown in FIG. 18. Form M displays the characteristic peaks of Family I and three sets of peaks, being set 1 at 2-theta of 11.2; set 2 at 2-theta of 14.0 and 14.6; set 3 at 2-theta of 15.9, 16.6, 17.1 and 17.5.

A representative PXRD pattern of Form N is shown in FIG. 10. Form N displays the characteristic peaks of Family I. The sets of peaks of form N are similar to those of forms F, G, J and M, being set 1 at 2-theta of 11.2 to 11.6; set 2 at 2-theta of 13.9 to 15.0; and set 3 at 2-theta of 15.9 to 17.9, with the peaks may vary slightly in position, intensity and width due to mixing of variable proportion of isomorphs in Family I.

A representative PXRD pattern of form Q is shown in FIG. 30. Form Q displays peaks at 2-theta of 6.8, 8.4 and 20.2 degree.

A representative PXRD pattern of form R is shown in FIG. 31.

Example 11

Single Crystal X-ray Analysis

Data were collected at room temperature using Bruker X-ray diffractometers equipped with copper radiation and graphite monochromators. Structures were solved using direct methods. The SHELXTL computer library provided by Bruker AXS, Inc facilitated all necessary crystallographic computations and molecular displays (SHELXTL™ Reference Manual, Version 5.1, Bruker AXS, Madison, Wis., USA (1997)).

Example 12

Calculation of PXRD Pattern from Single Crystal Data

To compare the results between a single crystal and a powder sample, a calculated powder pattern can be obtained from single crystal results. The XFOG and XPOW computer programs provided as part of the SHELXTL computer library were used to perform this calculation. Comparing the calculated powder pattern with the experimental powder pattern confirms whether a powder sample corresponds to an assigned single crystal structure (Table 9A). This procedure was performed on the crystal forms of azithromycin A, D, F, G, and J.

The calculated PXRD diffraction pattern of azithromycin form A is given in FIG. 1.

Figure 5:
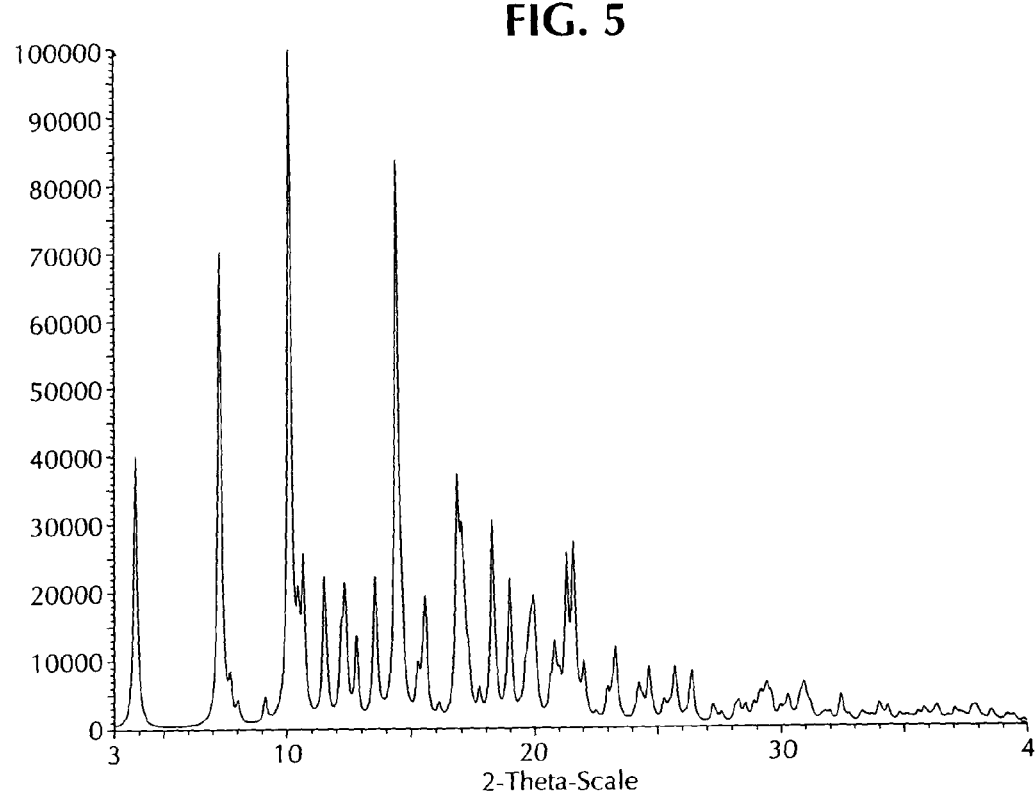
FIG. 5 is a calculated powder X-ray diffraction pattern of azithromycin form D. The scale of the abscissa is in degrees 2-theta (2θ). The ordinate is the intensity in counts.

The calculated PXRD diffraction pattern of azithromycin form D is given in FIG. 5.

Figure 9:
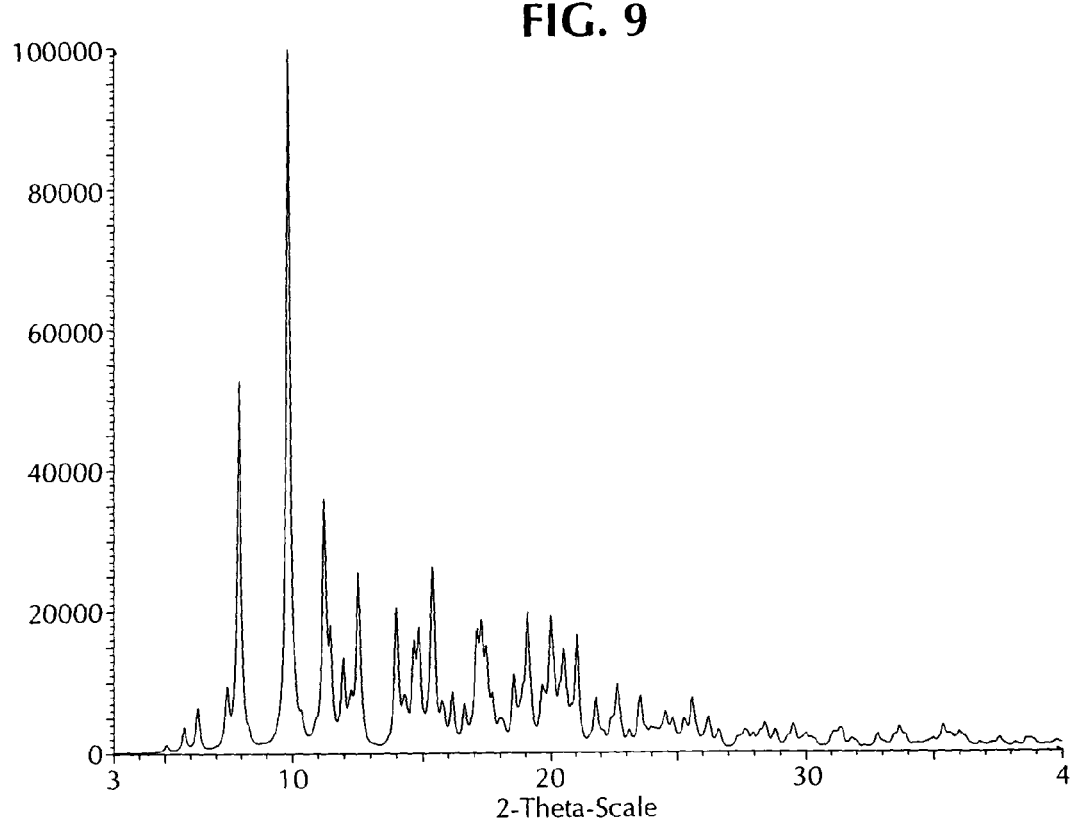
FIG. 9 is a calculated powder X-ray diffraction pattern of azithromycin form F. The scale of the abscissa is in degrees 2-theta (2θ). The ordinate is the intensity in counts.

The calculated PXRD diffraction pattern of azithromycin form F is given in FIG. 9.

Figure 12:
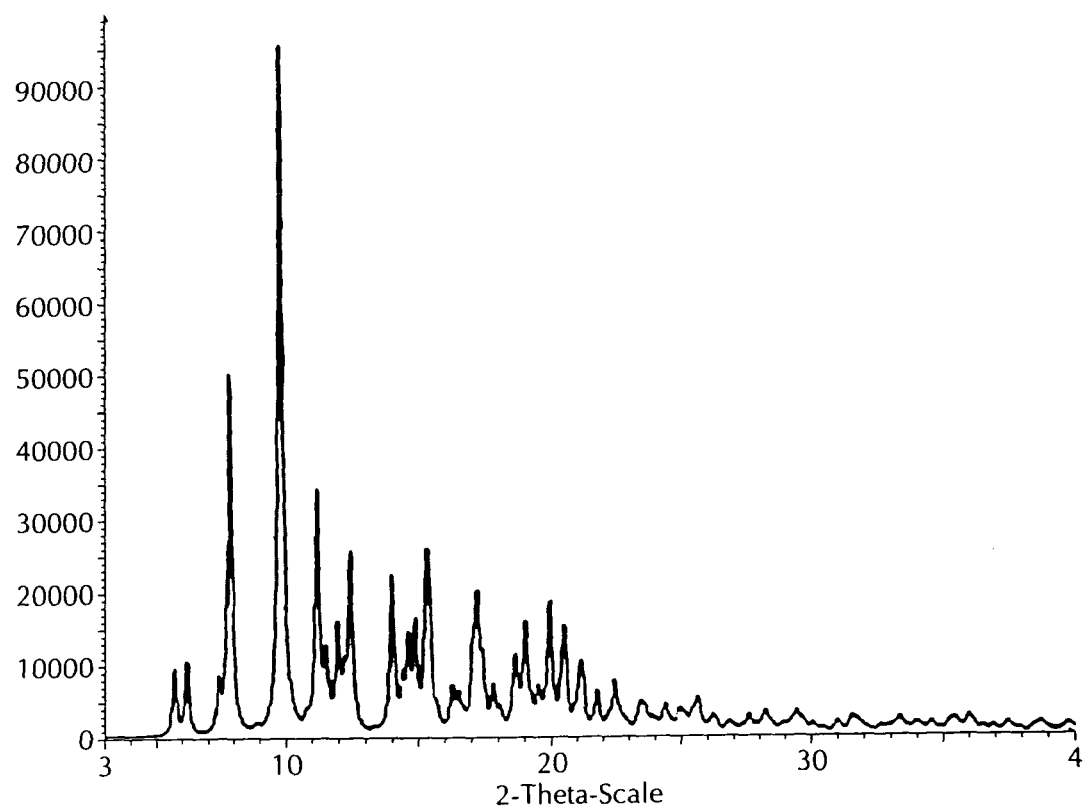
FIG. 12 is a calculated powder X-ray diffraction pattern of azithromycin form G. The scale of the abscissa is in degrees 2-theta (2θ). The ordinate is the intensity is counts.

The calculated PXRD diffraction pattern of azithromycin form G is given in FIG. 12.

Figure 15:
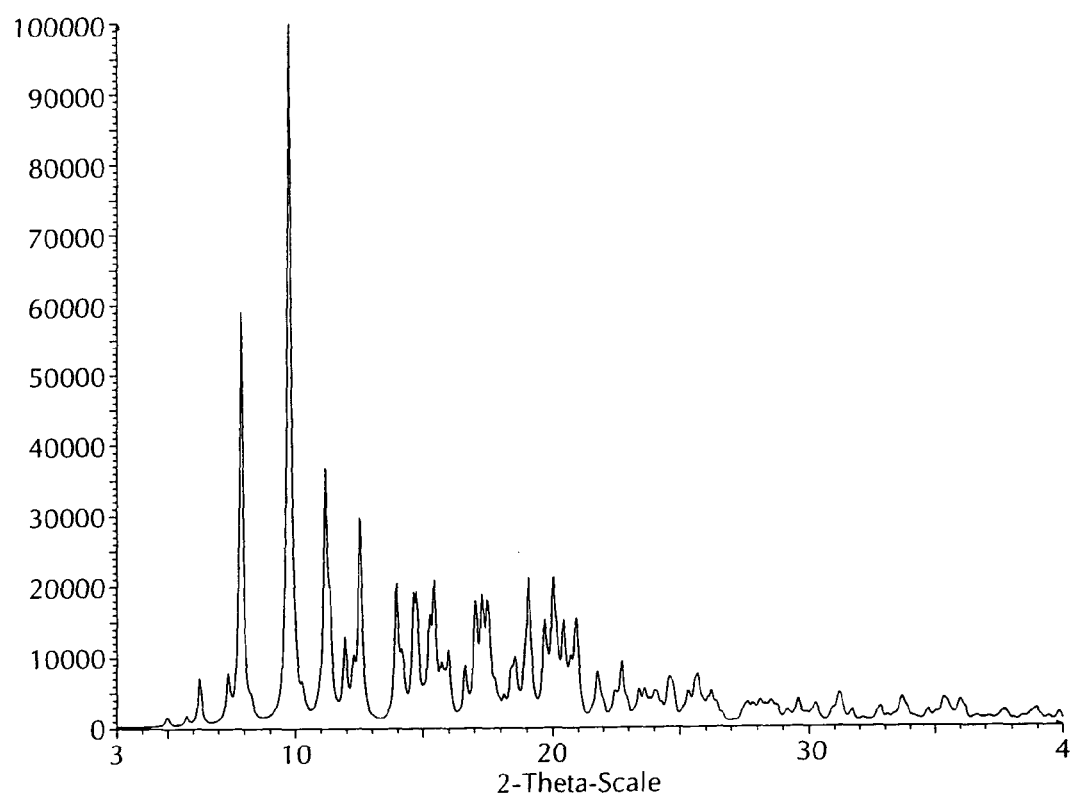
FIG. 15 is a calculated powder X-ray diffraction pattern of azithromycin form J. The scale of the abscissa is in degrees 2-theta (2θ). The ordinate is the intensity in counts.

The calculated PXRD diffraction pattern of azithromycin form J is given in FIG. 15.

The results are displayed in the overlaid powder X-ray diffraction patterns for forms A, D, F, G, and J in FIGS. 3, 7, 11, 14 and 17, respectively. The lower pattern corresponds to the calculated powder pattern (from single crystal results) and the upper pattern corresponds to a representative experimental powder pattern. A match between the two patterns indicated the agreement between powder sample and the corresponding single crystal structure.

perature and pressure. Depending on the quantity of sample analyzed, 7 mm BL or 4 mm BL Bruker probes were employed, accomodating 300 mg and 75 mg of sample with maximum speeds of 7 kHz and 15 kHz, respectively. Data were processed with an exponential line broadening function of 5.0 Hz. Proton decoupling of 65 kHz and 100 kHz were used with the 7mm and 4 mm probes, respectively. A sufficient number of acquisitions were averaged out to obtain adequate signal-to-noise ratios for all peaks. Typically, 600 scans were acquired with recycle delay of 3.0 s (seconds), corresponding approximately to a 30 minute total acquisition time. Magic angle was adjusted using KBr powder according to standard NMR vendor practices. The spectra were referenced relative to either the methyl reso-

TABLE 9A

Cacluated and Experimental PXRD Peaks of Isomorphs of Family I

| F calculated | F experimental | G calculated | G experimental | J calculated | J experimental | M experimental |
|---|---|---|---|---|---|---|
|  |  | 5.2 | 5.0 |  |  |  |
|  |  | 5.7 | 5.8 | 5.8 | 5.7 | 5.6 |
| 6.3 | 6.2 | 6.2 | 6.2 | 6.3 | 6.2 | 6.2 |
| 7.4 | 7.4 | 7.5 | 7.4 | 7.4 | 7.3 | 7.3 |
| 7.9 | 7.8 | 7.9 | 7.9 | 7.9 | 7.8 | 7.8 |
| 8.8 | 8.9 | 8.9 | 9.3 | 8.3 | 8.2 | 8.2 |
| 9.9 | 9.8 | 9.9 | 9.9 | 9.8 | 9.7 | 9.8 |
| 10.3 | 10.3 |  | 10.2 | 10.4 | 10.3 | 10.2 |
| 10.9 |  | 10.9 | 10.8 |  |  |  |
| 11.3 | 11.2 | 11.3 | 11.2 | 11.2 | 11.2 | 11.2 |
| 11.5 | 11.4 | 11.6 | 11.6 | 11.4 | 11.4 | missing |
| 12.0 | 11.9 | 12.0 | 11.9 | 12.0 | 11.9 | 11.9 |
| 12.3 | 12.2 | 12.3 |  | 12.3 | 12.3 | 12.2 |
| 12.6 | 12.5 | 12.5 | 12.5 | 12.6 | 12.5 | 12.5 |
| 14.0 | 14.0 | 13.4 | 13.3 | 14.0 | 13.9 | 14.0 |
| 14.3 | 14.3 | 14.1 | 14.0 | 14.2 | 14.2 | missing |
|  |  | 14.4 | 14.4 |  |  |  |
| 14.7 | 14.7 | 14.7 | 14.6 | 14.7 | 14.6 | 14.6 |
| 14.9 | 14.8 | 14.9 | 14.9 | 14.8 |  |  |
| 15.4 | 15.3 | 15.4 | 15.3 | 15.3 | 15.3 | 15.3 |
| 15.8 | 15.7 | 15.7 | 15.7 | 15.8 | 15.7 | 15.9 |
| 16.2 | 16.2 | 16.3 | 16.3 | 16.0 | 16.0 | missing |
| 16.6 | 16.6 | 16.6 | 16.6 | 16.7 | 16.6 | 16.6 |
| 17.1 | 17.2 | 17.1 |  | 17.1 | 17.0 | 17.1 |
| 17.3 | 17.3 | 17.3 | 17.2 | 17.4 | 17.2 | missing |
| 17.5 | 17.4 | 17.5 | 17.4 | 17.6 | 17.5 | 17.5 |
| 17.7 | 17.7 | 17.9 | 17.8 | 17.9 |  |  |
| 18.0 | 18.0 | 18.1 | 18.1 | 18.2 | 18.1 | 18.4 |
| 18.6 | 18.5 | 18.7 | 18.7 | 18.5 | 18.5 | 18.5 |
| 19.1 | 19.0 | 19.1 | 19.0 | 19.1 | 19.0 | 19.1 |
| 19.7 | 19.6 | 19.6 | 19.6 | 19.8 | 19.7 | 19.6 |
| 20.0 | 20.0 | 20.0 | 20.0 | 20.1 | 20.0 | 20.0 |
| 20.5 | 20.4 | 20.6 | 20.5 | 20.5 | 20.4 | 20.4 |
| 21.1 | 21.0 | 21.2 | 21.0 | 20.8 | 20.9 | 20.9 |
| 21.8 | 21.7 |  | 21.6 | 21.6 | 21.7 | 21.7 |
| 22.1 | 22.0 | 21.8 | 21.8 | 21.8 |  |  |
| 22.5 | 22.4 | 22.3 | 22.2 | 22.5 | 22.4 | 22.5 |
| 22.7 | 22.6 | 22.5 | 22.5 | 22.8 | 22.6 |  |
| 23.1 | 23.1 | 22.9 |  | 23.4 | 23.3 | 23.2 |
| 23.6 | 23.5 | 23.5 | 23.5 | 23.7 | 23.5 | 23.6 |

Example 13

Solid State NMR Analysis

Solid State NMR Analysis:

All $^{13}C$ solid state NMR spectra were collected on an 11.75 T spectrometer (Bruker Biospin, Inc., Billerica, Mass.), corresponding to 125 MHz $^{13}C$ frequency. The spectra were collected using a cross-polarization magic angle spinning (CPMAS) probe operating at ambient temnance of hexamethylbenzen (HMB) at 17.3 ppm or the upfield resonance of adamantane (ADM) at 29.5 ppm. HMB referenced spectra show chemical shifts of all peaks shifted down field by 0.08 ppm with respect to same spectra referenced to ADM. The spectral window minimally included the spectra region from 190 to 0 ppm. The results are summarized in Table 10. Ss-NMR spectra for forms M, H and R were referenced to ADM. Ss-NMR spectra for forms A, D, G, F, J and N were referenced to HMB. Forms H and R were spun at a rate of 15 kHz.

TABLE 10

$^{13}$C ss-NMR chemical shifts of Azithromycin (±0.2 ppm)

| A | D | G | F | J | M | N | H | R |
|---|---|---|---|---|---|---|---|---|
| 178.1 | 178.1 | 179.5* | 179.5 | 179.6 | 179.6 | 179.6 | 179.5 | 177.9 |
| 104.1 | 103.9 | 105.5 | 178.6 | 178.4 | 105.6 | 178.7 | 178.7 | 104.6 |
| 98.4 | 95.1 | 103.5 | 105.5 | 105.5 | 103.4 | 105.6 | 105.4 | 103.6 |
| 84.6 | 84.2 | 95.0 | 103.4 | 103.4 | 94.9 | 103.6 | 103.2 | 95.3 |
| 82.6 | 79.4 | 86.2 | 94.9 | 95.0 | 86.7 | 95.0 | 95.0 | 85.4 |
| 79.3 | 78.9 | 83.1 | 86.4 | 86.4 | 82.9 | 86.5 | 86.4 | 84.0 |
| 78.3 | 75.7 | 78.9 | 83.0 | 82.9 | 79.3 | 83.1 | 82.7 | 79.4 |
| 75.6 | 74.6 | 78.2 | 79.1 | 79.2 | 78.1 | 79.0 | 79.2 | 79.0 |
| 74.7 | 74.0 | 77.6 | 78.1 | 78.1 | 77.0 | 77.9 | 78.3 | 75.6 |
| 73.9 | 72.9 | 76.4 | 77.9 | 76.8 | 76.7 | 76.5 | 78.0 | 74.5 |
| 73.5 | 71.9 | 75.7 | 76.5 | 76.2 | 74.7 | 74.8 | 76.4 | 73.9 |
| 70.8 | 71.0 | 74.7 | 74.7 | 74.7 | 74.2 | 74.2 | 74.7 | 73.9 |
| 68.0 | 69.4 | 74.3 | 74.1 | 74.1** | 71.3 | 73.6 | 74.1 | 72.9 |
| 66.2 | 67.8 | 73.5 | 73.5 | 72.0 | 69.2 | 71.5 | 73.5 | 71.8 |
| 63.8 | 65.7 | 71.3 | 71.4 | 71.3 | 68.6 | 69.2 | 73.1 | 71.0 |
| 63.2 | 64.7 | 69.1 | 69.1 | 69.2 | 67.3 | 68.7 | 71.2 | 69.1 |
| 52.2 | 49.2 | 68.8 | 68.6 | 68.6 | 66.2 | 67.3 | 69.1 | 67.5 |
| 44.3 | 45.8 | 67.4 | 67.3 | 67.3** | 65.5 | 66.2 | 68.4 | 65.6 |
| 42.6 | 43.1 | 65.9 | 66.1 | 66.2** | 63.8 | 65.7 | 67.3 | 64.5 |
| 41.7 | 40.6 | 65.2 | 65.6 | 65.5** | 63.3 | 63.7 | 66.9 | 49.4 |
| 39.1 | 37.1 | 64.0 | 63.6 | 63.7 | 50.0 | *58.1* | 66.1 | 45.7 |
| 35.4 | 36.4 | 63.3 | *58.0* | 50.0 | 47.1 | 50.1 | 65.5* | 42.9 |
| 34.6 | 29.6 | 50.0 | 50.0 | 46.9 | 45.9 | 47.1 | 63.7* | 41.6 |
| 26.9 | 29.3 | 46.9 | 47.0 | 45.9 | 44.7 | 46.0 | 49.9 | 40.4 |
| 26.3 | 28.0 | 46.0 | 45.9 | 44.7 | 43.8 | 44.8 | 46.8 | 37.0 |
| 23.7 | 27.7 | 44.5 | 44.7 | 43.7 | 41.9 | 43.8 | 45.9 | 36.2 |
| 23.3 | 22.1 | 43.7 | 43.7 | 41.6 | 41.1 | 41.5 | 44.5 | 29.4 |
| 21.7 | 21.1 | 41.5 | 41.5 | 41.0 | 37.4 | 41.1 | 43.8* | 29.0 |
| 19.5 | 18.6 | 40.8 | 41.1 | 37.1 | 36.2 | 37.3 | 41.7 | 28.2 |
| 17.5 | 16.7 | 37.5 | 37.3 | 36.5** | 33.6 | 36.5 | 40.9 | 27.4 |
| 15.9 | 16.1 | 36.5 | 36.4 | 35.4** | 30.1 | 33.7 | 37.1 | 21.4 |
| 13.2 | 10.6 | 33.6 | 33.6 | 33.5 | 28.1 | 30.4 | 36.3 | 20.8 |
| 11.3 | 9.0 | 30.0 | 30.3 | 30.4 | 27.2 | 28.1 | 33.7 | 18.7 |
| 7.2 | 8.6 | 27.9 | 28.0 | 28.0 | *26.0* | 27.2 | 33.3 | 16.5 |
|  |  | 27.3 | 27.1 | 27.1 | 23.2 | *26.0* | 30.5* | 16.1 |
|  |  | 23.1 | 23.2 | *25.2* | 22.8 | 23.2 | 27.9 | 15.7 |
|  |  | 22.5 | 22.6 | 23.2 | 22.5 | 22.6 | 27.1 | 10.3 |
|  |  | 21.9 | 21.9 | 22.5 | 21.8 | 22.0 | 23.1 | 9.6** |
|  |  | 20.9 | 20.8 | 21.9 | 20.2 | 20.8 | 22.6 | 8.9** |
|  |  | 0.2 | 20.4 | 20.7 | 18.9 | 19.0 | 22.3 | 8.6 |
|  |  | 18.8 | 18.9 | 18.9 | 17.4 | 16.9 | 21.9 |  |
|  |  | 17.0 | 16.8 | 16.8 | 16.3 | 15.8 | 20.7 |  |
|  |  | 16.0 | *17.2* | 15.6** | 15.5 | 12.2 | 20.3 |  |
|  |  | 12.2 | 15.7 | 12.1 | 12.1 | 9.9 | 18.8 |  |
|  |  | 10.4 | 12.2 | *11.5* | 10.3 | 9.4 | 17.1 |  |
|  |  | 9.9 | 10.1 | 12.1 | 9.6 | 7.9 | 16.6 |  |
|  |  | 9.3 | 9.8 | 10.0 | 9.3 | 6.6 | 15.8 |  |
|  |  | 7.6 | 9.3 | 9.3 | 7.7 |  | 15.4 |  |
|  |  | 6.5 | 7.9 | 8.1 | 7.1 |  | 12.0 |  |
|  |  |  | 6.6 | 6.8 |  |  | 9.9** |  |
|  |  |  |  |  |  |  | 9.1 |  |
|  |  |  |  |  |  |  | 7.9 |  |
|  |  |  |  |  |  |  | 7.0 |  |

The chemical shifts labeled in bold and underlined are the peaks or sets of peaks representative of each form. The chemical shifts labeled in italic are the solvent peaks that may be broad and variable (±0.4ppm). The chemical shifts labeled with single asterisk may show splitting of <0.3 ppm. The chemical shifts labeled with double asterisks may show variation of ±0.3 ppm The chemical shifts reported are accurate to within ±0.2 ppm unless otherwise indicated.

Figure 21:
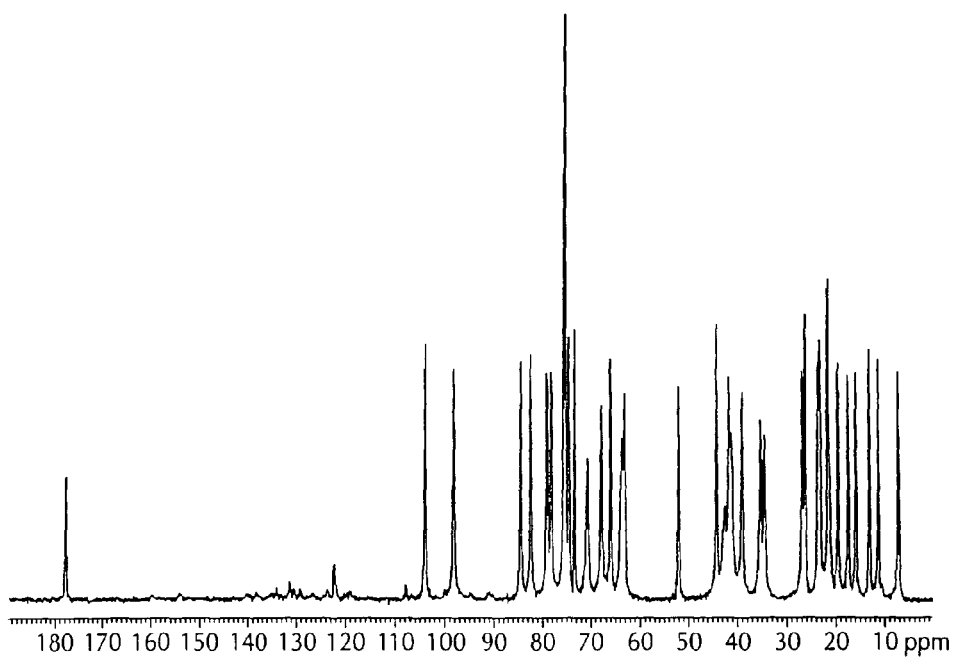
FIG. 21 is a $^{13}$C solid state NMR spectrum of azithromycin form A.

A representative $^{13}$C ssNMR spectrum of form A is shown in FIG. 21. Form A displays a peak at 178.1 ppm, and peaks at 104.1, 98.4, 84.6, 26.9, 13.2, 11.3 and 7.2 ppm.

Figure 22:
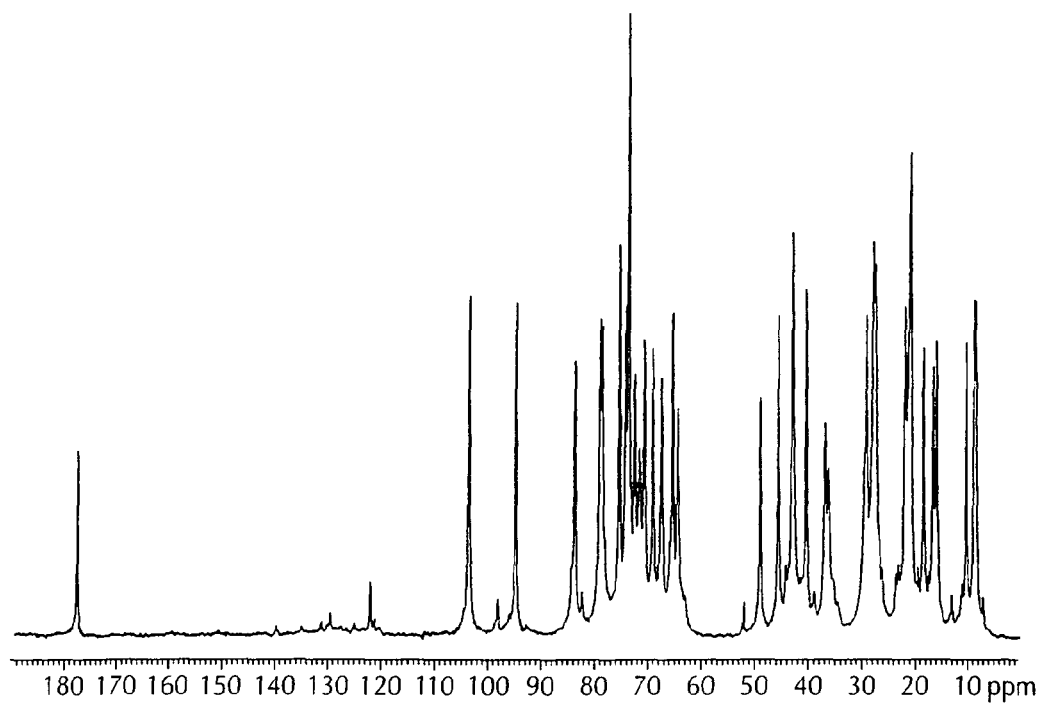
FIG. 22 is a $^{13}$C solid state NMR spectrum of azithromycin form D.

A representative $^{13}$C ssNMR spectrum of form D is shown in FIG. 22. Form D displays the highest chemical shift peak of 178.1 ppm and peaks at chemical shifts of 103.9, 95.1, 84.2, 10.6, 9.0 and 8.6 ppm.

Figure 23:
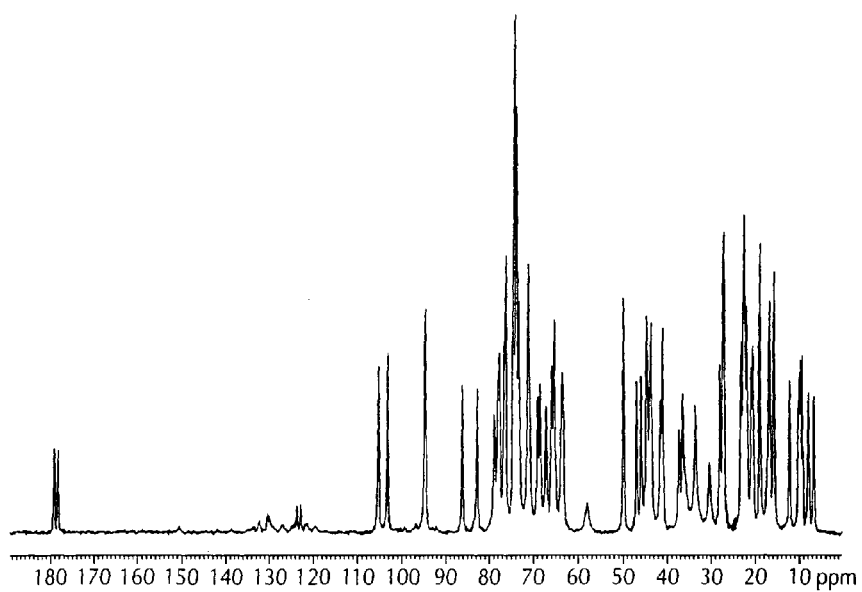
FIG. 23 is a $^{13}$C solid state NMR spectrum of azithromycin form F.

A representative $^{13}$C ssNMR spectrum of form F is shown in FIG. 23. Form F has two chemical shift peaks at approximately 179.1±2 ppm, being 179.5 ppm and 178.6 ppm, and a set of 5 peaks at 10.1, 9.8, 9.3, 7.9, and 6.6 ppm, and ethanol peaks at 58.0±0.5 ppm and 17.2±0.5 ppm. The solvent peaks can be broad and relatively weak in intensity.

Figure 24:
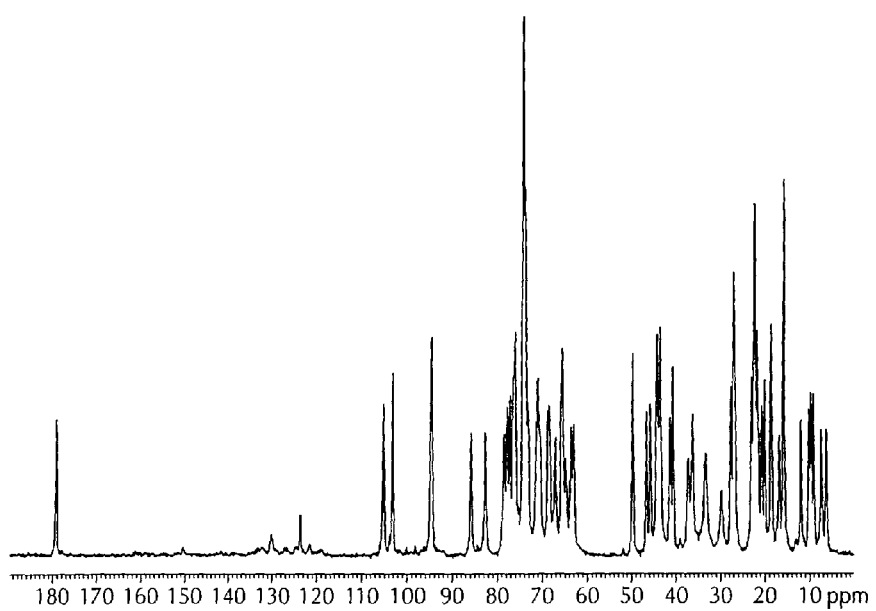
FIG. 24 is a $^{13}$C solid state NMR spectrum of azithromycin form G.

A representative $^{13}$C ssNMR spectrum of form G is shown in FIG. 24. Form G has the highest chemical shift peak of 179.5 ppm, being a single peak with possible splitting of <0.3 ppm and a set of 5 peaks at 10.4, 9.9, 9.3, 7.6, 6.5 ppm.

Figure 25:
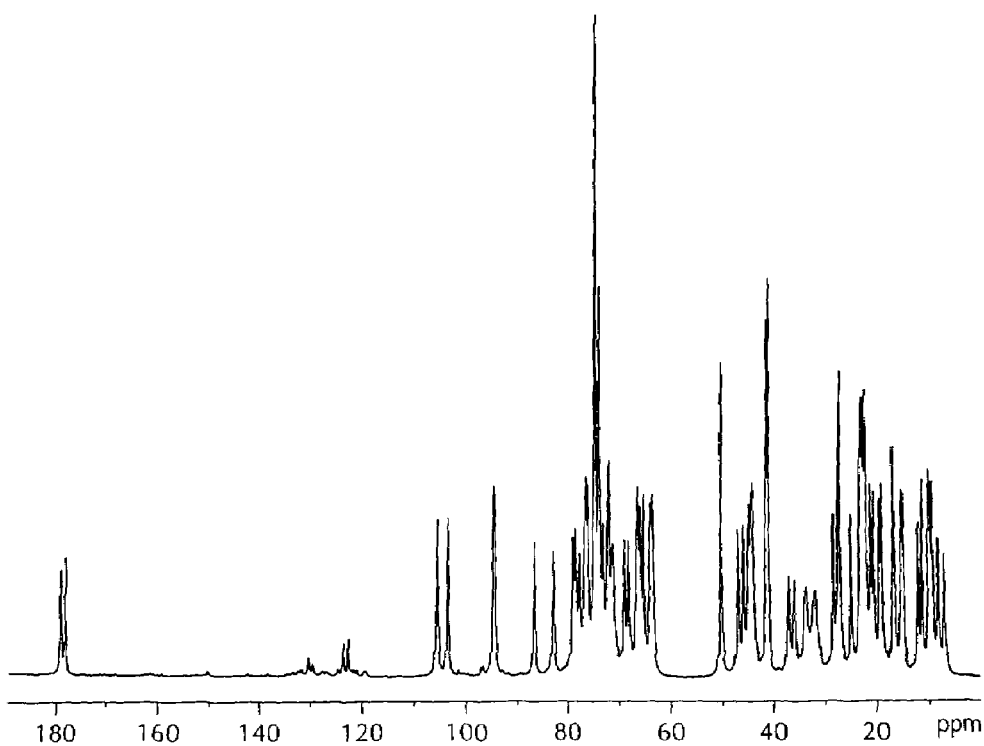
FIG. 25 is a $^{13}$C solid state NMR spectrum of azithromycin form J.

A representative $^{13}$C ssNMR spectrum of form J is shown in FIG. 25. Form J has two chemical shift peaks at approximately 179.1±2 ppm, those being 179.6 ppm and 178.4 ppm, a set of 4 peaks at 10.0, 9.3, 8.1 and 6.8 ppm and n-propanol peaks at 11.5±0.5 ppm and 25.2±0.5 ppm. The solvent peak can be broad and relatively weak in intensity.

Figure 26:
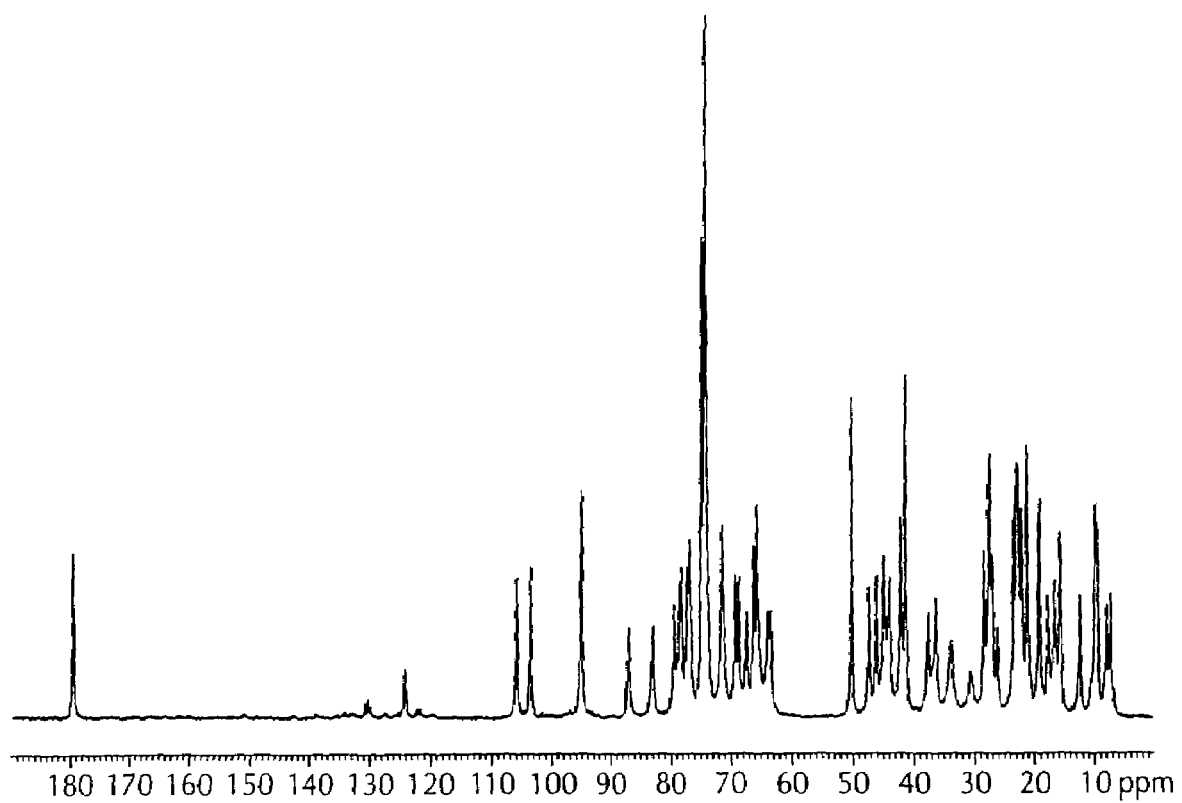
FIG. 26 is a $^{13}$C solid state NMR spectrum of azithromycin form M.

A representative $^{13}$C ssNMR spectrum of form M is shown in FIG. 26. Form M has one chemical shift peak at 179±1 ppm, being 179.6 ppm, peaks at 41.9, and 16.3 ppm, a set of 5 peaks at 10.3, 9.6, 9.3, 7.7 and 7.1 ppm and an isopropanol peak at 26.0±0.5 ppm. The solvent peak can be broad and relatively weak in intensity.

Figure 27:
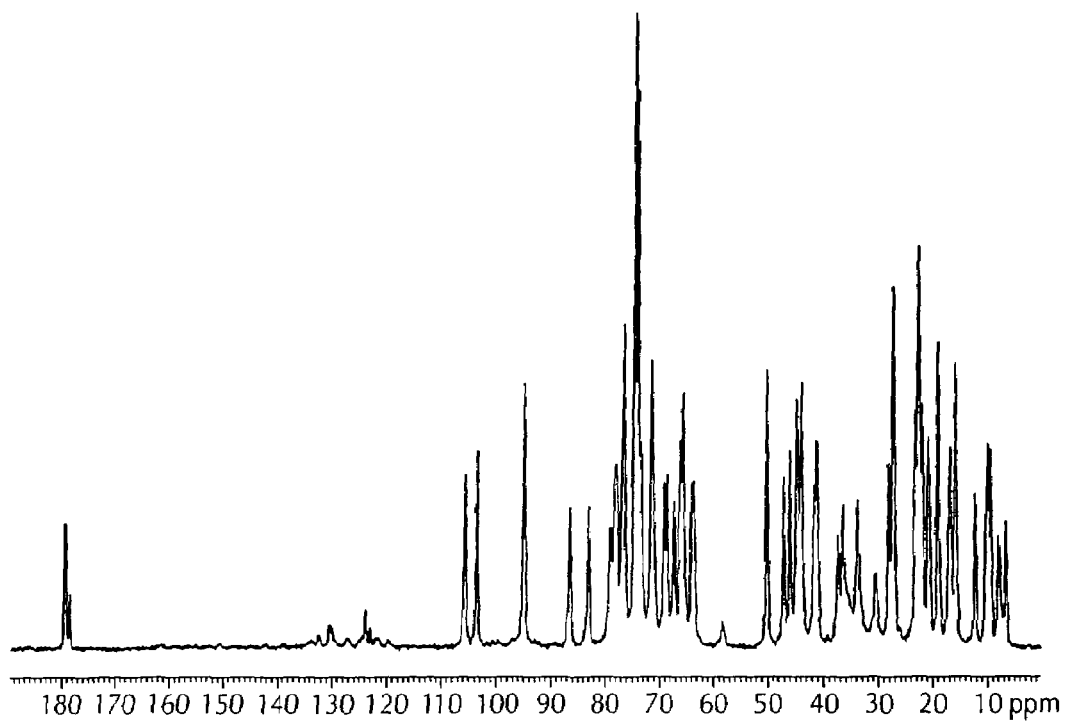
FIG. 27 is a $^{13}$C solid state NMR spectrum of azithromycin form N.

A representative $^{13}$C ssNMR spectrum of form N is shown in FIG. 27. Form N displays chemical shifts as a combination of isomorphs in Family I. The peaks may vary in chemical shift and in relative intensities and width due to the mixing of variable proportion of isomorphs contained in the form N crystalline solid solution.

Figure 28:
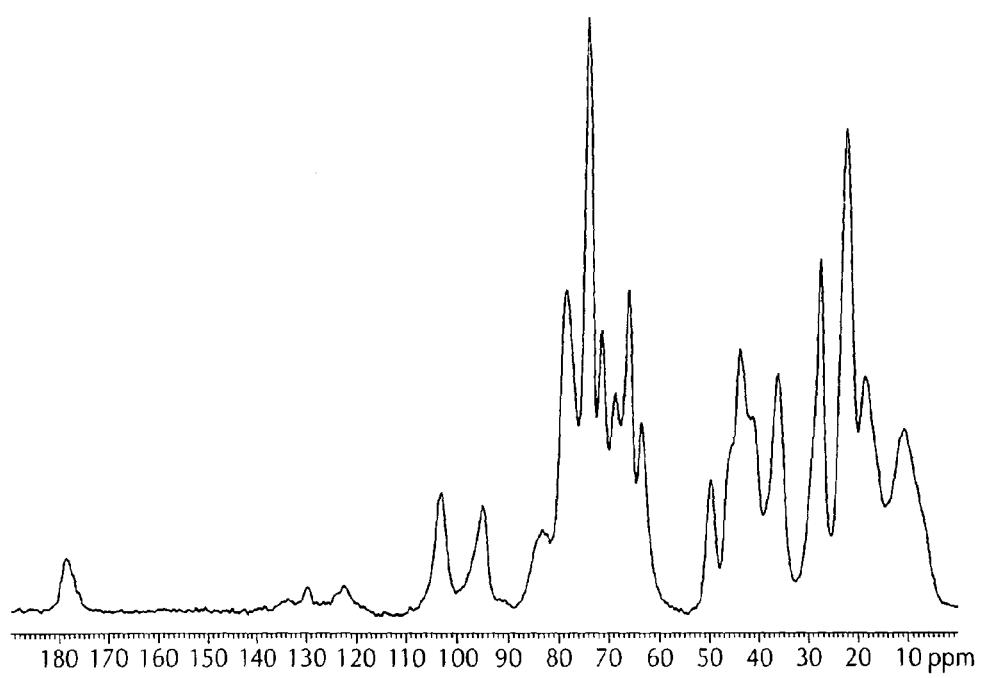
FIG. 28 is a $^{13}$C solid state NMR spectrum of amorphous azithromycin.

A representative $^{13}$C ssNMR spectrum of amorphous form is shown in FIG. 28. The amorphous azithromycin displays broad chemical shifts. The characteristic chemical shifts have the peak positions at 179 and 11±0.5 ppm.

A summary of the observed ssNMR peaks for forms A, D, F, G, H, J, M, N and R azithromycin is given in Table 10.

Example 14

NMR Analysis of a Dosage Form

To demonstrate the ability of $^{13}$C ssNMR to identify the form of azithromycin contained in a pharmaceutical dosage form, coated azithromycin tablets containing form G azithromycin were prepared and analyzed by $^{13}$C ssNMR. Tablets were wet granulated and tabletted on an F-Press (Manesty, Liverpool, UK) using 0.262"×0.531" tooling. Tablets were formulated and tabletted to contain 250 mg of form G azithromycin with a total tablet weight of 450 mg using the formula given below. The tablets were uniformly coated with pink Opadry II® (mixture of lactose monohydrate, hydroxypropylmethylcellulose, titanium dioxide, Drug & Cosmetic red #30, and triacetin) (Colorcon, West Point, Pa.).

| Material | Percentage | Batch(g) |
| --- | --- | --- |
| Azithromycin form "G" | 58.23 | 174.69 |
| Pregellatinized corn starch | 6.00 | 18.00 |
| Anhydrous dicalcium phosphate | 30.85 | 92.55 |
| Sodium croscarmelose | 2.00 | 6.00 |
| Magnesium stearate with 10% sodium laurel sulfate | 2.92 | 8.76 |
| Total | 100.00 | 300.00 |

A coated tablet was gently crushed and the powdered sample was packed with a packing tool in solid state rotor containing no $^{13}$C background. Analysis of the sample was performed under conditions outlined in Example 13.

Figure 29:
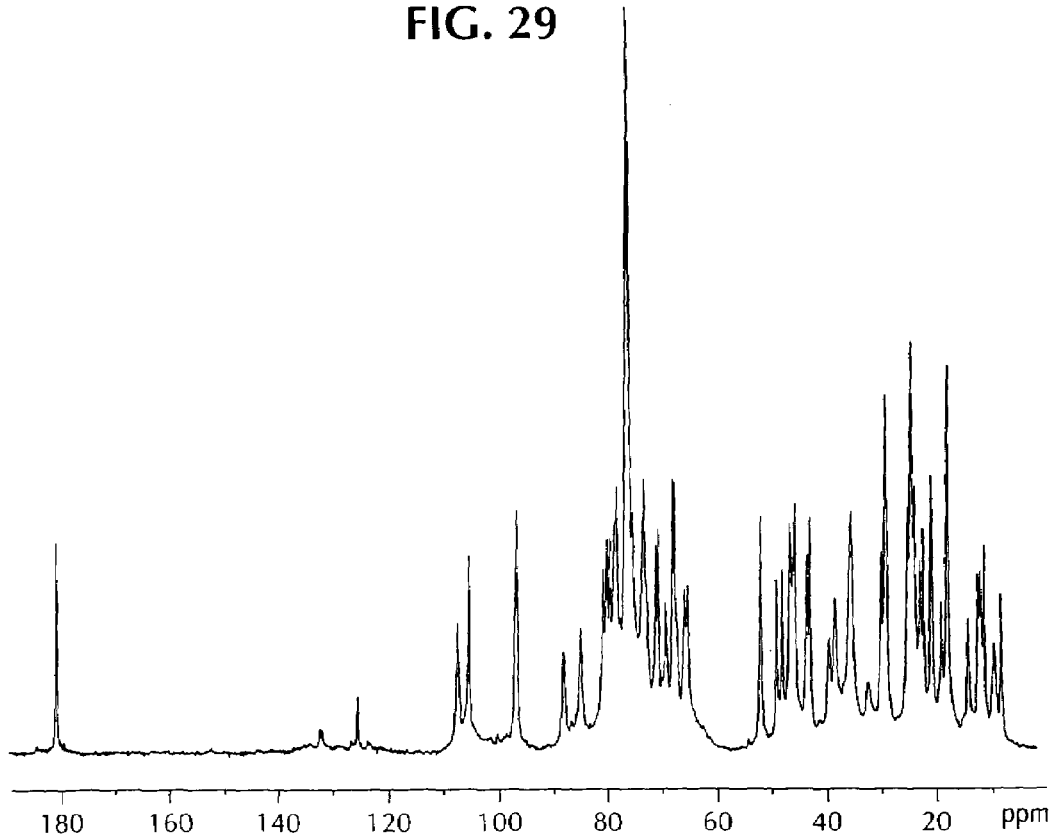
FIG. 29 is a $^{13}$C solid state NMR spectrum of a pharmaceutical tablet containing form G azithromycin.

A representative $^{13}$C ssNMR spectrum of the tablet containing form G azithromycin is given in FIG. 29.

Example 15

Antimicrobial Activity:

The activity of the crystal forms of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition; Aprroved Standard*, published by The National Committee for Clinical Laboratory Standards (NCCLS) guidelines; the minimum inhibitory concentration (MIC) is used to compare strains. The crystalline compound is initially dissolved in dimethylsulfoxide (DMSO) as 40 mg/ml stock solution.

| Strain Designation | Macrolide Resistance Mechanism(s) |
| --- | --- |
| *Staphylococcus aureus* 1116 | susceptible parent |
| *Staphylococcus aureus* 1117 | ErmB |
| *Staphylococcus aureus* 0052 | susceptible parent |
| *Staphylococcus aureus* 1120 | ErmC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ErmB |
| *Streptococcus pyogenes* 1062 | susceptible parent |
| *Streptococcus pyogenes* 1061 | ErmB |
| *Streptococcus pyogenes* 1064 | ErmB |
| *Streptococcus agalactiae* 1024 | susceptible parent |
| *Streptococcus agalactiae* 1023 | ErmB |
| *Streptococcus pneumoniae* 1016 | Susceptible |
| *Streptococcus pneumoniae* 1046 | ErmB |

-continued

| Strain Designation | Macrolide Resistance Mechanism(s) |
|---|---|
| Streptococcus pneumoniae 1095 | ErmB |
| Streptococcus pneumoniae 1175 | MefE |
| Streptococcus pneumoniae 0085 | Susceptible |
| Haemophilus influenzae 0131 | Susceptible |
| Moraxella catarrhalis 0040 | Susceptible |
| Moraxella catarrhalis 1055 | erythromycin intermediate resistance |
| Escherichia coli 0266 | Susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compound is prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the crystal forms of the present invention can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection that would be lethal in the absence of drug treatment.

The crystal forms of the present invention (hereinafter "the active compound(s)"), may be administered through oral, parenteral, topical, or rectal routes in the treatment or prevention of bacterial or protozoa infections. In general, the active compound is most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 2 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compound may be administered alone or in combination with pharmaceutically acceptable carriers or diluents by the routes previously indicated, and such administration may be carried out in single or multiple doses. More particularly, the active compound may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, sachets, powders for oral suspension, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compound is present in such dosage forms at concentration levels ranging from about 1.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compound topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compound may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

What is claimed is:

1. An azithromycin mixture comprising substantially pure azithromycin monohydrate hemi-ethanol solvate characterized as having a plurality of $^{13}C$ solid state NMR peaks with at least two peaks at approximately 179.5±0.2 ppm and 178.6±0.2 ppm and optionally less than 10% by weight of azithromycin dihydrate characterized as having at least three $^{13}C$ solid state NMR peaks at approximately 13.2 ppm, 11.3 ppm and 7.2 ppm; wherein said substantially pure azithromycin monohydrate hemi-ethanol solvate contains less than 10% of alternative polymorphic or isomorphic crystalline forms of azithromycin by weight.

2. The azithromycin mixture of claim 1, wherein said $^{13}C$ solid state NMR spectrum further comprises a peak with chemical shift of about 58.0 ppm.

3. The azithromycin mixture of claim 2, wherein said $^{13}C$ solid state NMR spectrum further comprises a peak with chemical shift of about 17.2 ppm.

4. The azithromycin mixture of claim 3, wherein said $^{13}C$ solid state NMR spectrum further comprises a peak with chemical shift of about 10.1 ppm.

5. The azithromycin mixture of claim 4, wherein said $^{13}C$ solid state NMR spectrum further comprises a peak with chemical shift of about 9.8 ppm.

6. The azithromycin mixture of claim 5, wherein said $^{13}C$ solid state NMR spectrum further comprises a peak wit chemical shift of about 9.3 ppm.

7. The azithromycin mixture of claim 6, wherein said $^{13}C$ solid state NMR spectrum further comprises a peak with chemical shift of about 7.9 ppm.

8. The azithicinycin mixture of claim 7, wherein said $^{13}C$ solid state NMR spectrum further comprises a peak wit chemical shift of about 6.6 ppm.

9. The azitbromycin mixture of claim 1 wherein said substantially pure azithromycin monohydrate hemi-ethanol solvate contains less than 5% of alternative polymorphic or isomorphic crystalline forms of azithromycin by weight.

10. The azithromycin mixture of claim 1 wherein said substantially pure azithromycin monohydrate hemi-ethanol solvate contains less than 1% of alternative polymorphic or isomorphic crystalline forms of azithromycin by weight.

11. The azithromycin mixture of claim 1 wherein said azithromycin mixture optionally contains less than 5% of azithromycin dihydrate by weight.

12. The azithromycin mixture of claim 1 wherein said azithromycin mixture optionally contains less than 1% of azithromycin dihydrate by weight.

* * * * *